(12) United States Patent
Ho

(10) Patent No.: US 12,220,193 B2
(45) Date of Patent: Feb. 11, 2025

(54) HAPTIC FEEDBACK FOR ALIGNING ROBOTIC ARMS

(71) Applicant: Auris Health, Inc., Santa Clara, CA (US)

(72) Inventor: Mingyen Ho, Santa Clara, CA (US)

(73) Assignee: Auris Health, Inc., Santa Clara, CA (US)

( * ) Notice: Subject to any disclaimer, the term of this patent is extended or adjusted under 35 U.S.C. 154(b) by 524 days.

(21) Appl. No.: 17/485,228

(22) Filed: Sep. 24, 2021

(65) Prior Publication Data

US 2022/0096183 A1 Mar. 31, 2022

Related U.S. Application Data

(63) Continuation of application No. PCT/IB2021/058612, filed on Sep. 21, 2021.
(Continued)

(51) Int. Cl.
*A61B 34/32* (2016.01)
*B25J 13/02* (2006.01)
*A61B 34/00* (2016.01)
*A61B 34/37* (2016.01)
*B25J 9/16* (2006.01)

(52) U.S. Cl.
CPC ............. *A61B 34/32* (2016.02); *B25J 13/025* (2013.01); *A61B 34/37* (2016.02); *A61B 34/76* (2016.02); *B25J 9/161* (2013.01); *B25J 9/1664* (2013.01)

(58) Field of Classification Search
CPC ......... A61B 34/32; A61B 34/37; A61B 34/76; B25J 13/025
See application file for complete search history.

(56) References Cited

U.S. PATENT DOCUMENTS 10,434,660 B2 10/2019 Meyer et al.
10,464,209 B2 11/2019 Ho et al.
(Continued)

FOREIGN PATENT DOCUMENTS

CN 101227870 A 7/2008
CN 102612350 A 7/2012
(Continued)

OTHER PUBLICATIONS

CN Office Action for Appl. No. 202180065312.9, dated Oct. 21, 2023.
(Continued)

*Primary Examiner* — Catherine M Voorhees
(74) *Attorney, Agent, or Firm* — Paradice & Li LLP

(57) ABSTRACT

Techniques relate to aligning one or more robotic arms of a robotic system to one or more alignment positions. For example, resistance for manual movement of a robotic arm can be set based on a direction of movement of a distal end of the robotic arm with respect to one or more alignment positions. The robotic arm can provide a first amount of resistance for manual movement in a direction closer to the one or more alignment positions and to provide a second amount of resistance for manual movement in a direction away from the one or more alignment positions. In some instances, the robotic arm can be automatically moved to the one or more alignment positions when the robotic arm is within a distance to the one or more alignment positions.

30 Claims, 10 Drawing Sheets

Related U.S. Application Data

(60) Provisional application No. 63/083,664, filed on Sep. 25, 2020.

(56) References Cited

U.S. PATENT DOCUMENTS

| | | | |
|---|---|---|---|
| 11,280,690 B2 | 3/2022 | Lin et al. | |
| 11,701,783 B2 | 7/2023 | Meyer et al. | |
| 2004/0034282 A1* | 2/2004 | Quaid, III | A61B 34/20 600/300 |
| 2011/0270271 A1 | 11/2011 | Nowlin et al. | |
| 2013/0116706 A1 | 5/2013 | Lee et al. | |
| 2013/0345872 A1* | 12/2013 | Brooks | B25J 9/1676 700/264 |
| 2015/0366624 A1* | 12/2015 | Kostrzewski | A61B 34/76 606/130 |
| 2018/0078320 A1* | 3/2018 | Griffiths | A61B 34/77 |
| 2018/0221039 A1 | 8/2018 | Shah | |
| 2019/0105785 A1* | 4/2019 | Meyer | G05B 19/00 |
| 2020/0078097 A1* | 3/2020 | Gregerson | B25J 9/1666 |
| 2020/0197108 A1 | 6/2020 | Usui | |
| 2020/0253678 A1 | 8/2020 | Hulford et al. | |
| 2020/0281676 A1 | 9/2020 | Rohs et al. | |
| 2020/0289050 A1 | 9/2020 | Barrera et al. | |

FOREIGN PATENT DOCUMENTS

| | | |
|---|---|---|
| CN | 109640860 A | 4/2019 |
| CN | 111328306 A | 6/2020 |
| WO | 2006124390 A2 | 11/2006 |
| WO | 2011041428 A2 | 4/2011 |
| WO | 2018039268 A1 | 3/2018 |
| WO | 2019074670 A1 | 4/2019 |
| WO | 2020181290 A1 | 9/2020 |

OTHER PUBLICATIONS

Search Report for appl No. PCT/IB2021/058612, dated Dec. 21, 2021, 13 pages.
Written Opinion for appl No. PCT/IB2021/058612, dated Dec. 21, 2021, 4 pages.
Supplementary European Search Report, issued on Sep. 10, 2024, in European Patent Application No. 21871781.7, 10 pages.
Third Office Action, dated Nov. 7, 2024, from China Patent Application No. 202180065312.9, 16 pages.

* cited by examiner

HAPTIC FEEDBACK FOR ALIGNING ROBOTIC ARMS

RELATED APPLICATION(S)

This application is a continuation of International Application No. PCT/IB2021/058612, filed Sep. 21, 2021 and entitled HAPTIC FEEDBACK FOR ALIGNING ROBOTIC ARMS, which claims the benefit of priority to U.S. Provisional Application No. 63/083,664, filed Sep. 25, 2020, and entitled HAPTIC FEEDBACK FOR ALIGNING ROBOTIC ARMS, the disclosures of which are hereby incorporated by reference in their entirety.

BACKGROUND

Field

The present disclosure relates to the field of medical devices and procedures.

Description of Related Art

Various medical procedures involve the use of one or more medical instruments to investigate and/or treat patients. In some cases, multiple systems/devices are implemented to control a medical instrument to perform a procedure on a patient. The improper use of such systems, devices, and/or medical instruments can adversely affect the health of the patient and/or efficacy of the procedure.

SUMMARY

In some implementations, the present disclosure relates to a system comprising a robotic arm configured to couple to a medical instrument, and control circuitry communicatively coupled to the robotic arm. The control circuitry is configured to determine one or more alignment positions for a distal end of the robotic arm. Further, the control circuitry is configured to set a resistance for manual movement of the robotic arm based at least in part on a direction of movement of the distal end of the robotic arm with respect to the one or more alignment positions.

In some embodiments, the one or more alignment positions include a plurality of alignment positions associated with alignment to a distal end of an additional robotic arm of the system. The plurality of alignment positions may be associated with a virtual rail associated with at least one of insertion or retraction of the medical instrument. Further, in some embodiments, the one or more alignment positions may represent a previous position of the distal end of the robotic arm.

In some embodiments, the control circuitry is further configured to determine that manual movement of the robotic arm has ceased for more than a period of time, determine that the distal end of the robotic arm is positioned within a threshold distance to the one or more alignment positions, and automatically move the robotic arm to the one or more alignment positions based at least in part on determining that manual movement of the robotic arm has ceased for more than the period of time and determining that the distal end of the robotic the robotic arm is positioned within the threshold distance to the one or more alignment positions.

In some embodiments, the control circuitry is configured to set the resistance for manual movement of the robotic arm by setting a first resistance for manual movement of the robotic arm in a direction closer to the one or more alignment positions with respect to at least one dimension, and setting a second resistance for manual movement of the robotic arm in a direction away from the one or more alignment positions with respect to at least one dimension. The second resistance may be greater than the first resistance. Further, in some embodiments, the control circuitry may be further configured to determine that the distal end of the robotic arm has reached the one or more alignment positions, and increase the second resistance for manual movement of the robotic arm in the direction away from the one or more alignment positions with respect to at least one dimension. Moreover, in some embodiments, the one or more alignment positions include a plurality of alignment positions associated with alignment to a distal end of an additional robotic arm of the system. The control circuitry may be further configured to determine that the distal end of the robotic arm has reached a first alignment position of the plurality of alignment positions, and set a third resistance for manual movement of the robotic arm from the first alignment position to a second alignment position of the plurality of alignment positions. The third resistance may be less than the first resistance.

In some embodiments, the control circuitry is configured to set the resistance for manual movement of the robotic arm by decreasing the resistance as the robotic arm moves closer to the one or more alignment positions. Moreover, in some embodiments, the control circuitry is configured to set the resistance for manual movement of the robotic arm by increasing the resistance as the robotic arm moves farther from the one or more alignment positions.

In some implementations, the present disclosure relates to one or more non-transitory computer-readable media storing computer-executable instructions that, when executed by control circuitry, cause the control circuitry to perform operations comprising determining one or more alignment positions for a distal end of a robotic arm that is configured to couple to a medical instrument, and configuring the robotic arm to provide a first amount of resistance for manual movement in a direction closer to the one or more alignment positions and to provide a second amount of resistance for manual movement in a direction away from the one or more alignment positions.

In some embodiments, the operations further comprise determining that manual movement of the robotic arm has ceased for more than a period of time, determining that the distal end of the robotic arm is positioned within a threshold distance to the one or more alignment positions, and automatically moving the robotic arm to the one or more alignment positions based at least in part on the determining that the manual movement of the robotic arm has ceased for more than the period of time and the determining that the distal end of the robotic the robotic arm is positioned within the threshold distance to the one or more alignment positions.

In some embodiments, the operations further comprise determining that the robotic arm is moving farther from the one or more alignment positions with respect to at least one dimension, and increasing the second amount of resistance for manual movement of the robotic arm in the direction away from the one or more alignment positions. Further, in some embodiments, the operations further comprise determining that the distal end of the robotic arm has reached the one or more alignment positions, and increasing the second amount of resistance for manual movement of the robotic arm in the direction away from the one or more alignment positions.

In some embodiments, the one or more alignment positions include a plurality of alignment positions associated with alignment to a distal end of an additional robotic arm. The operations further comprise determining that the distal end of the robotic arm has reached a first alignment position of the plurality of alignment positions, and configuring the robotic arm to provide a third amount of resistance for manual movement of the robotic arm from the first alignment position to a second alignment position of the plurality of alignment positions. The third resistance may be less than the first amount of resistance.

In some implementations, the present disclosure relates to a robotic system comprising control circuitry configured to determine one or more alignment positions, and a robotic arm communicatively coupled to the control circuitry. The robotic arm is configured to couple to a medical instrument, provide a first amount of resistance for manual movement of the robotic arm in a direction closer to the one or more alignment positions, and provide a second amount of resistance for manual movement of the robotic arm in a direction farther from the one or more alignment positions.

In some embodiments, the one or more alignment positions include a plurality of alignment positions representing a virtual rail associated with at least one of insertion or retraction of the medical instrument. Further, in some embodiments, the one or more alignment positions represent a previous position of a distal end of the robotic arm.

In some embodiments, the control circuitry is further configured to determine that manual movement of the robotic arm has ceased for more than a period of time, determine that a distal end of the robotic arm is positioned within a threshold distance to the one or more alignment positions, and cause the robotic arm to automatically move to the one or more alignment positions. Further, in some embodiments, the control circuitry is further configured to determine that a distal end of the robotic arm has reached the one or more alignment positions, and increase the second amount of resistance for manual movement of the robotic arm in the direction away from the one or more alignment positions.

In some embodiments, the one or more alignment positions include a plurality of alignment positions associated with alignment to a distal end of an additional robotic arm of the system. The control circuitry may be further configured to determine that a distal end of the robotic arm has reached a first alignment position of the plurality of alignment positions. Further, the robotic arm may be configured to provide a third amount of resistance for manual movement of the robotic arm from the first alignment position to a second alignment position of the plurality of alignment positions. The third resistance may be less than the first amount of resistance.

In some embodiments, the control circuitry is configured decrease the first amount of resistance as the robotic arm moves closer to the one or more alignment positions. Further, in some embodiments, the control circuitry is configured increase the second amount of resistance as the robotic arm moves farther from the one or more alignment positions.

In some implementations, the present disclosure relates to a method comprising determining, by control circuitry, one or more alignment positions for a distal end of a robotic arm that is configured to couple to a medical instrument, determining, by the control circuitry, a direction of manual movement of the robotic arm with respect to the one or more alignment positions, and configuring, by the control circuitry, an amount of resistance for the manual movement of the robotic arm based at least in part on the direction of the manual movement of the robotic arm with respect to the one or more alignment positions.

In some embodiments, the one or more alignment positions include a plurality of alignment positions associated with alignment to a distal end of an additional robotic arm. Further, in some embodiments, the one or more alignment positions represent a previous position of the distal end of the robotic arm.

In some embodiments, the method further comprises determining that the manual movement of the robotic arm has ceased for more than a period of time, determining that the distal end of the robotic arm is positioned within a threshold distance to the one or more alignment positions, and automatically moving the robotic arm to the one or more alignment positions based at least in part on the determining that the manual movement of the robotic arm has ceased for more than the period of time and the determining that the distal end of the robotic the robotic arm is positioned within the threshold distance to the one or more alignment positions.

In some embodiments, the determining the direction of the manual movement of the robotic arm includes determining that the robotic arm is moving farther from the one or more alignment positions with respect to at least one dimension. The configuring the amount of resistance for the manual movement of the robotic arm may include configuring a first amount of resistance for the manual movement of the robotic arm. The first amount of resistance may be more than a second amount of resistance associated with manual movement of the robotic arm closer to the one or more alignment positions.

In some embodiments, the determining the direction of the manual movement of the robotic arm includes determining that the robotic arm is moving closer to the one or more alignment positions with respect to at least one dimension. The configuring the amount of resistance for the manual movement of the robotic arm includes configuring a first amount of resistance for the manual movement of the robotic arm. The first amount of resistance may be less than a second amount of resistance associated with manual movement of the robotic arm farther from the one or more alignment positions.

In some embodiments, the amount of resistance is a first amount of resistance The method may further comprise determining that the distal end of the robotic arm has reached the one or more alignment positions, and configuring a second amount of resistance for manual movement of the robotic arm away from the one or more alignment positions. The second amount of resistance being greater than the first amount of resistance.

In some embodiments, the one or more alignment positions include a plurality of alignment positions associated with alignment to a distal end of an additional robotic arm. The amount of resistance may be a first amount of resistance. The method may further comprise determining that the distal end of the robotic arm has reached a first alignment position of the plurality of alignment positions, and configuring a second amount of resistance for manual movement of the robotic arm from the first alignment position to a second alignment position of the plurality of alignment positions. The second amount of resistance may be less than the first amount of resistance.

For purposes of summarizing the disclosure, certain aspects, advantages and features have been described. It is to be understood that not necessarily all such advantages may be achieved in accordance with any particular embodiment.

Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
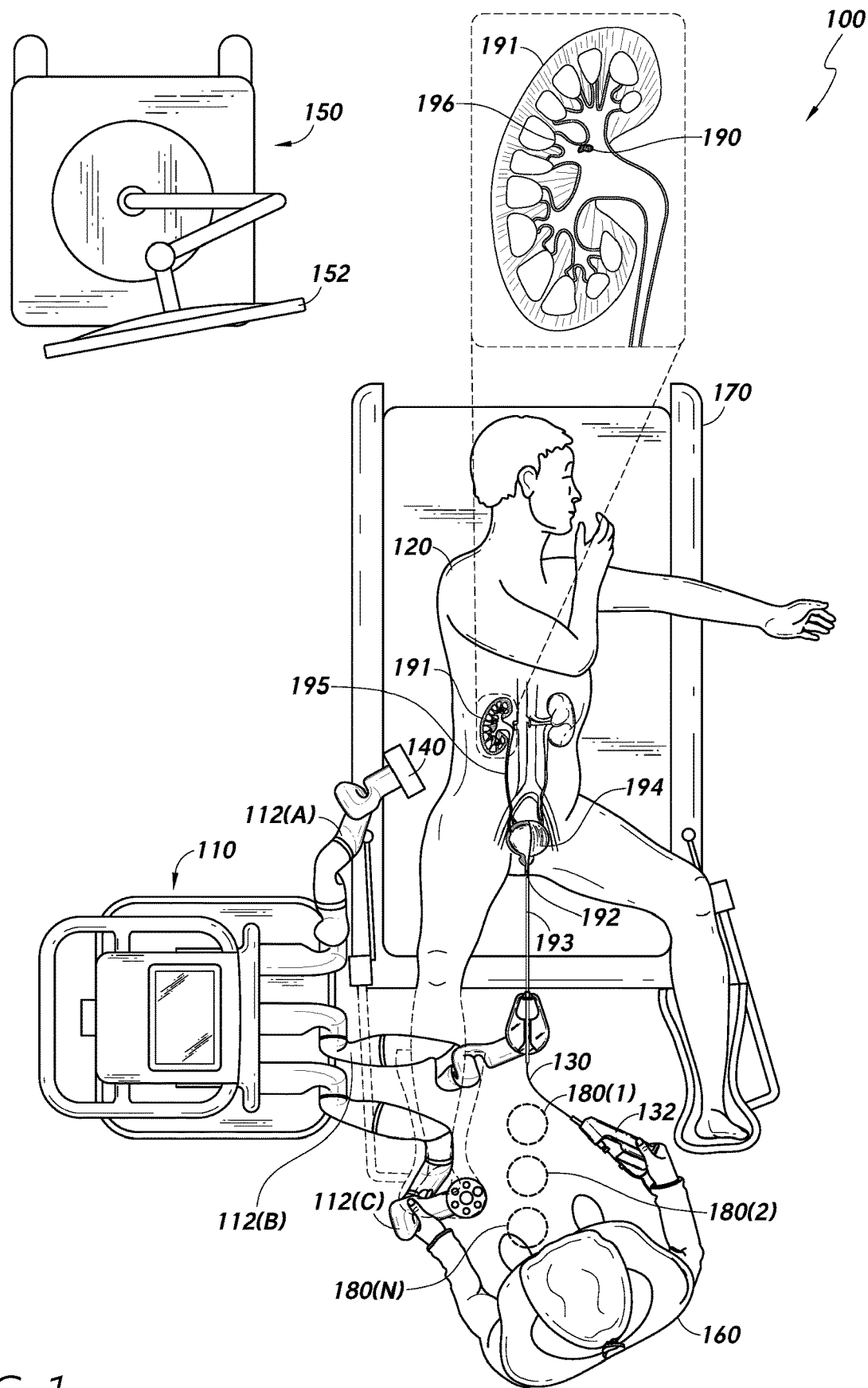
FIG. 1 illustrates an example medical system for performing various medical procedures in accordance with one or more embodiments.

The headings provided herein are for convenience only and do not necessarily affect the scope or meaning of the disclosure. Although certain embodiments and examples are disclosed below, subject matter extends beyond the specifically disclosed embodiments to other alternative embodiments and/or uses and to modifications and equivalents thereof. Thus, the scope of the claims that may arise here from is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location can be used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/ element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

Certain medical procedures involve the use of a robotic system to engage with and/or control one or more medical instruments. To accommodate various procedures, workflows, environments, physician preferences, and/or safety precautions, the robotic system can be positioned in different manners by a user. For example, the robotic system can include one or more robotic arms that are independently movable, so that a user can manually position the one or more robotic arms at a desired location to perform a procedure. Such manual movement can help avoid safety risks associated with automatic movement of the one or more robotic arms. However, such flexibility can make it difficult to accurately position the robotic arm at a desired location. For example, in some procedures, a first robotic arm may need to be aligned with a second robotic arm within a relatively small degree of tolerance (and/or with a particular amount of offset) to operate in a cooperative manner with the second robotic arm. Here, it may be difficult for a user to manually align the first robotic arm with the second robotic arm, such as to visualize an aligned configuration. Further, in some instances, a user may perform multiple tasks while attempting to position a robotic arm, such as positioning the robotic arm with one hand while holding a medical instrument in another hand. This can create additional difficulty in accurately positioning the robotic arm at a desired location.

The present disclosure relates to systems, devices, and methods to assist in positioning one or more robotic arms. For example, a robotic system can include one or more robotic arms that are configured to couple to one or more medical instruments to perform a procedure. At any time before, during, or after the procedure, a user can manually move a robotic arm in an attempt to position a distal end of the robotic arm at a particular position, such as a position aligned with another robotic arm, a previous position of the robotic arm, and so on. In some instances, the robotic system can provide haptic feedback to assist the user in aligning the robotic arm with a position. For example, the robotic arm can provide varying amounts of resistance for manual movement of the robotic arm to indicate if the robotic arm is moving closer to or farther from an alignment position, if the robotic arm is positioned at an alignment position, and so on. As such, the techniques discussed herein can enable a user to manually move a robotic arm (which can accommodate certain workflows, environments, physician preferences, and/or safety precautions) and accurately position the robotic arm at a particular location. This can provide the user with flexibility to move robotic arms out of and/or into a workspace at various times to provide adequate space for other tasks that do not involve the robotic arms, such as manual tasks performed by the user, tasks performed by other devices/instruments, etc. Further, in some instances, a robotic arm can be automatically moved to an alignment position, such as when the robotic arm is manually moved within proximity to the alignment position. This can further assist the physician in aligning the robotic arm.

Although certain aspects of the present disclosure are described herein in the context of renal, urological, and/or nephrological procedures, such as kidney stone removal/treatment procedures, it should be understood that such context is provided for convenience, and the concepts disclosed herein are applicable to any suitable medical procedure. For example, the following description is also applicable to other surgical/medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal. However, as mentioned, description of the renal/urinary anatomy and associated medical issues and procedures is presented below to aid in the description of the concepts disclosed herein.

Example Medical System

FIG. 1 illustrates an example medical system 100 for performing various medical procedures in accordance with aspects of the present disclosure. The medical system 100 includes a robotic system 110 configured to engage with and/or control one or more medical instruments and/or another device/instrument to perform a procedure on a patient 120. In the example of FIG. 1, the robotic system 110 couples to a scope 130 and an electromagnetic (EM) field generator 140, as discussed in further detail below. The medical system 100 also includes a control system 150 configured to interface with the robotic system 110, provide information regarding the procedure, and/or perform a variety of other operations. For example, the control system 150 can include a display(s) 152 to present certain information to assist a physician 160. The medical system 100 can include a table 170 (e.g., bed) configured to hold the patient 120. Various acts are described herein as being performed by the physician 160. These acts can be performed directly by the physician 160, a user under the direction of the physician 160, another user (e.g., a technician), a combination thereof, and/or any other user. The devices/components of the medical system 100 can be arranged in a variety of ways depending on the particular procedure.

The control system 150 can be coupled to the robotic system 110 and operate in cooperation with the robotic system 110 to perform a medical procedure on the patient 120. For example, the control system 150 can communicate with the robotic system 110 via a wireless or wired connection to control a medical instrument connected to the robotic system 110, receive an image(s) captured by a medical instrument (e.g., the scope 130), and so on. Additionally, or alternatively, the control system 150 can provide fluids to the robotic system 110 via one or more fluid channels, provide power to the robotic system 110 via one or more electrical connections, provide optics to the robotic system 110 via one or more optical fibers or other components, and so on. In some embodiments, the control system 150 can communicate with a medical instrument to receive sensor data (via the robotic system 110 and/or directly from the medical instrument). Sensor data can indicate or be used to determine a position and/or orientation of the medical instrument. Further, in some embodiments, the control system 150 can communicate with the table 170 to position the table 170 in a particular orientation or otherwise control the table 170. Moreover, in some embodiments, the control system 150 can communicate with the EM field generator 140 to control generation of an EM field around the patient 120.

The robotic system 110 can include one or more robotic arms 112 configured to engage with and/or control a medical instrument(s) and/or another device/instrument. Each robotic arm 112 can include multiple arm segments coupled to joints, which can provide multiple degrees of movement. A distal end of a robotic arm 112 (e.g., end effector) can be configured to couple to an instrument/device. In the example of FIG. 1, the second robotic arm 112(B) is coupled to a portion of the scope 130, which can be inserted and/or navigated within the patient 120 to investigate and/or treat a target site. The third robotic arm 112(C) can also be coupled to a handle 132 of the scope 130, such as upon aligning the third robotic arm 112(C), as discussed in further detail below. Further, the robotic arm 112(A) is coupled to the EM field generator 140, which can be configured to generate an EM field that is detected by a sensor on a medical instrument, such as the scope 130. The EM field generator 140 can generally be positioned near a treatment site during a phase of a procedure (e.g., within a particular distance). Although three robotic arms are illustrated in FIG. 1 as connected to particular medical instruments, the robotic system 110 can include any number of robotic arms that are configured to connect to various types of medical instruments.

The robotic system 110 can be communicatively coupled to any component of the medical system 100. For example, the robotic system 110 can be communicatively coupled to the control system 150 to receive a control signal from the control system 150 to perform an operation, such as to control a robotic arm 112 in a particular manner, manipulate a medical instrument, and so on. Further, the robotic system 110 can be configured to receive an image (also referred to as image data) from the scope 130 depicting internal anatomy of the patient 120 and/or send the image to the control system 150, which can then be displayed on the display(s) 152. Moreover, the robotic system 110 can be coupled to a component of the medical system 100, such as the control system 150, in a manner as to allow for fluids, optics, power, or the like to be received therefrom.

The robotic system 110 and/or the control system 150 can be configured to assist in positioning one or more of the robotic arms 112 at a desired location(s), such as at one or more of a plurality of alignment positions 180(1)-(N) (with N being an integer greater than 1). In some embodiments, the robotic system 110 can be configured to provide haptic feedback in the form of resistance for manual movement to assist the physician 160 in aligning one or more of the robotic arms 112. The amount of resistance for a robotic arm 112 can based on a direction in which the robotic arm 112 is being moved, a proximity of the robotic arm 112 to an alignment position, and so on. The amount of resistance can affect a force experienced by the physician 160 when moving the robotic arm 112. For example, the control system 150 and/or the robotic system 110 can configure the third robotic arm 112(C) to provide a first amount of resistance for manual movement in a direction closer to the alignment positions 180, causing the physician 160 to experience a feeling of lightness (or heaviness, in the alternative) when moving the third robotic arm 112(C), in comparison to movement in a direction away from the alignment positions 180. Further, the control system 150 and/or the robotic system 110 can configure the third robotic arm 112(C) to provide a second amount of resistance for manual movement in a direction away from the alignment positions 180, causing the physician 160 to experience a feeling of heaviness (or lightness, in the alternative) when moving the third robotic arm 112(C), in comparison to movement in a direction closer to the alignment positions 180.

In some embodiments, the robotic system 110 and/or control system 150 can reconfigure an amount of resistance for a robotic arm 112 when the robotic arm 112 reaches an alignment position. For example, assume that the third robotic arm 112(C) is configured to provide a first amount of resistance for manual movement in a direction closer to the alignment positions 180 and a second amount of resistance for manual movement away from the alignment positions 180. When the third robotic arm 112(C) reaches an alignment position 180, the third robotic arm 112(C) can be configured to provide a lesser (or greater, in some cases) amount of resistance (in comparison to the first amount of resistance) for manual movement of the third robotic arm 112(C) from one of the alignment positions 180 to another one of the alignment positions 180. Further, the third robotic arm 112(C) can be configured to provide an even greater (or lesser, in some cases) amount of resistance (in comparison to the second amount of resistance) for manual movement of the third robotic arm 112(C) away from any of the alignment positions 180. As such, the physician 160 can experience a change in resistance when the third robotic arm 112(C) transitions from an unaligned position to an alignment position 180, such that the robotic arm 112(C) feels as if it is locking into place at the alignment position. Further, the physician 160 can experience a feeling of even greater lightness/ease when manually moving the third robotic arm 112(C) from one of the alignment positions 180 to another one of the alignment positions 180.

In some embodiments, the robotic system 110 and/or the control system 150 can control a robotic arm 112 to automatically move to an alignment position. For example, if the physician 160 manually moves the distal end of the third robotic arm 112(C) within proximity to the alignment position 180(1), and releases the third robotic arm 112(C), the robotic system 110 and/or the control system 150 can automatically move the third robotic arm 112(C) to the alignment position 180(1) if the third robotic arm 112(C) is within a predetermined distance to the alignment position 180(1). In some cases, the third robotic arm 112(C) can be automatically aligned when manual movement of the third robotic arm 112(C) has ceased for more than a period of time (e.g., a predetermined period of time), which can be based on releasing a button to control manual movement of the third robotic arm 112(C), as discussed in further detail below.

An alignment position can represent any type of determined/desired position. In some embodiments, an alignment position for a robotic arm is associated with alignment to a distal end of another robotic arm. For example, in the example of FIG. 1, the alignment positions 180 for the third robotic arm 112(C) represent positions associated with alignment to a distal end of the second robotic arm 112(B), so that the scope 130 (when attached to the third robotic arm 112(C)) is able to be inserted/retracted along a substantially straight virtual rail, as discussed in further detail below. Further, in some embodiments, an alignment position can represent a previous position of a distal end of a robotic arm. For example, assume that the third robotic arm 112(C) is initially positioned at a position 180(2) with or without the handle 132 of the scope 130 connected to the third robotic arm 112(C), and then subsequently moved to the side with or without detaching the scope 130 (e.g., to provide additional workspace). If the physician 160 desires to return the third robotic arm 112(C) to the position 180(2) to continue the procedure with the scope 130 or a different medical instrument, the physician 160 can realign the end of the third robotic arm 112(C) to the position 180(2) using the alignment techniques discussed herein and/or reattach the scope 130/another medical instrument to the third robotic arm 112(C). Moreover, in some embodiments, an alignment position can be associated with alignment to anatomy of a patient. For example, the alignment positions 180 can be located along a longitudinal axis that is aligned with a urethra of the patient 120. For ease of illustration, the alignment positions 180 are illustrated with three representations. However, any number of alignment positions can be implemented.

A medical instrument can include a variety of types of instruments, such as a scope (sometimes referred to as an "endoscope"), a catheter, a needle, a guidewire, a lithotripter, a basket retrieval device, forceps, a vacuum, a needle, a scalpel, an imaging probe, jaws, scissors, graspers, needle holder, micro dissector, staple applier, tacker, suction/irrigation tool, clip applier, and so on. A medical instrument can include a direct entry instrument, percutaneous entry instrument, and/or another type of instrument. In some embodiments, a medical instrument is a steerable device, while in other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

The term "scope" or "endoscope" are used herein according to their broad and ordinary meanings and can refer to any type of elongate medical instrument having image generating, viewing, and/or capturing functionality (or configured to provide such functionality with an imaging device deployed though a working channel) and configured to be introduced into any type of organ, cavity, lumen, chamber, and/or space of a body. For example, a scope or endoscope, such as the scope 130, can refer to a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), a borescope, and so on. A scope/endoscope, in some instances, may comprise a rigid or flexible tube, and may be dimensioned to be passed within an outer sheath, catheter, introducer, or other lumen-type device, or may be used without such devices. In some embodiments, a scope includes one or more working channels through which additional tools, such as lithotripters, basketing devices, forceps, laser devices, imaging devices, etc., can be introduced into a treatment site.

The terms "direct entry" or "direct access" are used herein according to their broad and ordinary meaning and may refer to any entry of instrumentation through a natural or artificial opening in a patient's body. For example, the scope 130 may be referred to as a direct access instrument, since the scope 130 enters into the urinary tract of a patient via the urethra.

The terms "percutaneous entry" or "percutaneous access" are used herein according to their broad and ordinary meaning and may refer to entry, such as by puncture and/or minor incision, of instrumentation through the skin of a patient and any other body layers necessary to reach a target anatomical location associated with a procedure (e.g., the calyx network of the kidney). As such, a percutaneous access instrument may refer to a medical instrument, device, or assembly that is configured to puncture or to be inserted through skin and/or other tissue/anatomy, such as a needle, scalpel, guidewire, sheath, shaft, scope, catheter, and the like. However, it should be understood that a percutaneous access instrument can refer to other types of medical instruments in the context of the present disclosure. In some embodiments, a percutaneous access instrument refers to an instrument/device that is inserted or implemented with a device that facilitates a puncture and/or minor incision through the skin of a patient. For example, a catheter may be referred to as a percutaneous access instrument when the catheter is inserted through a sheath/shaft that has punctured the skin of a patient.

In some embodiments, a medical instrument includes a sensor (sometimes referred to as a position sensor) that is configured to generate sensor data. In examples, sensor data can indicate a position and/or orientation of the medical instrument and/or can be used to determine a position and/or orientation of the medical instrument. For instance, sensor data can indicate a position and/or orientation of a scope, which can include a roll of a distal end of the scope. A position and orientation of a medical instrument can be referred to as a pose of the medical instrument. A sensor can be positioned on a distal end of a medical instrument and/or any other location. In some embodiments, a sensor can provide sensor data to the control system 150, the robotic system 110, and/or another system/device to perform one or more localization techniques to determine/track a position and/or an orientation of a medical instrument.

In some embodiments, a sensor can include an electromagnetic (EM) sensor with a coil of conductive material. Here, an EM field generator, such as the EM field generator 140, can provide an EM field that is detected by the EM sensor on the medical instrument. The magnetic field can induce small currents in coils of the EM sensor, which can be analyzed to determine a distance and/or angle/orientation between the EM sensor and the EM field generator. Further, a sensor can include another type of sensor, such as a camera, a range sensor, a radar device, a shape sensing fiber, an accelerometer, a gyroscope, an accelerometer, a satellite-based positioning sensor (e.g., a global positioning system (GPS)), a radio-frequency transceiver, and so on.

In some embodiments, the medical system 100 can also include an imaging device (not illustrated in FIG. 1) which can be integrated into a C-arm and/or configured to provide imaging during a procedure, such as for a fluoroscopy-type procedure. The imaging device can be configured to capture/generate one or more images of the patient 120 during a procedure, such as one or more x-ray or CT images. In examples, images from the imaging device can be provided in real-time to view anatomy and/or medical instruments within the patient 120 to assist the physician 160 in performing a procedure. The imaging device can be used to perform a fluoroscopy (e.g., with a contrast dye within the patient 120) or another type of imaging technique.

The various components of the medical system 100 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Further, in some embodiments, the components of the medical system 100 are connected for data communication, fluid/gas exchange, power exchange, and so on, via one or more support cables, tubes, or the like.

In various examples, the medical system 100 is implemented to perform a medical procedure relating to the renal anatomy. The kidneys generally comprise two bean-shaped organs located on the left and right in the retroperitoneal space. In adult humans, the kidneys are generally about 11 cm in length. The kidneys receive blood from the paired renal arteries; blood exits into the paired renal veins. Each kidney is attached to a ureter, which is a tube that carries excreted urine from the kidney to the bladder. The bladder is attached to the urethra.

The kidneys are typically located relatively high in the abdominal cavity and lie in a retroperitoneal position at a slightly oblique angle. The asymmetry within the abdominal cavity, caused by the position of the liver, typically results in the right kidney being slightly lower and smaller than the left, and being placed slightly more to the middle than the left kidney. On top of each kidney is an adrenal gland. The upper parts of the kidneys are partially protected by the 11th and 12th ribs. Each kidney, with its adrenal gland is surrounded by two layers of fat: the perirenal fat present between renal fascia and renal capsule and pararenal fat superior to the renal fascia.

The kidney participates in the control of the volume of various body fluid compartments, fluid osmolality, acid-base balance, various electrolyte concentrations, and removal of toxins. The kidneys provide filtration functionality by secreting certain substances and reabsorbing others. Examples of substances secreted into the urine are hydrogen, ammonium, potassium, and uric acid. In addition, the kidneys also carry out various other functions, such as hormone synthesis, and others.

A recessed area on the concave border of the kidney is the renal hilum, where the renal artery enters the kidney and the renal vein and ureter leave. The kidney is surrounded by tough fibrous tissue, the renal capsule, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney is divided into two major structures: the outer renal cortex and the inner renal medulla. These structures take the shape of a plurality of cone-shaped renal lobes, each containing renal cortex surrounding a portion of medulla called a renal pyramid. Between the renal pyramids are projections of cortex called renal columns. Nephrons, the urine-producing functional structures of the kidney, span the cortex and medulla. The initial filtering portion of a nephron is the renal corpuscle, which is located in the cortex. This is followed by a renal tubule that passes from the cortex deep into the medullary pyramids. Part of the renal cortex, a medullary ray is a collection of renal tubules that drain into a single collecting duct.

The tip, or papilla, of each pyramid empties urine into a respective minor calyx; minor calyces empty into major calyces, and major calyces empty into the renal pelvis, which transitions to the ureter. At the hilum, the ureter and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis and calyces and separates these structures from the renal medullary tissue.

In some embodiments, the medical system 100 can be used to treat kidney stones. Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, uric acid, cysteine, and/or other compounds or combinations thereof.

Generally, there are several methods for treating patients with kidney stones, including observation, medical treatments (such as expulsion therapy), non-invasive treatments (such as extracorporeal shock wave lithotripsy (ESWL)), and surgical treatments (such as ureteroscopy and percutaneous nephrolithotomy ("PCNL)). In surgical approaches (e.g., ureteroscopy and PCNL), the physician gains access to the pathology (i.e., the object to be removed; e.g., the stone), the stone is broken into smaller pieces or fragments, and the relatively small stone fragments/particulates are mechanically extracted from the kidney.

To remove urinary stones from the bladder and ureter, surgeons may insert a ureteroscope into the urinary tract through the urethra. Typically, a ureteroscope includes an endoscope at its distal end configured to enable visualization of the urinary tract. The ureteroscope can also include a lithotripsy device to capture or break apart urinary stones. During a ureteroscopy procedure, one physician/technician may control the position of the ureteroscope, while another other physician/technician may control the lithotripsy device(s). In order to remove relatively large stones from the kidneys (i.e., "kidney stones"), physicians may use a percutaneous nephrolithotomy ("PCNL") technique that involves inserting a nephroscope through the skin (i.e., percutaneously) and intervening tissue to provide access to the treatment site for breaking-up and/or removing the stone(s).

In several of the examples described herein, robotic-assisted percutaneous procedures can be implemented in connection with various medical procedures, such as kidney stone removal procedures, wherein robotic tools (e.g., one or more components of the medical system 100) can enable a physician/urologist to perform endoscopic (e.g., ureteroscopy) target access as well as percutaneous access/treatment. This disclosure, however, is not limited to kidney stone removal and/or robotic-assisted procedures. In some implementations, robotic medical solutions can provide relatively higher precision, superior control, and/or superior hand-eye coordination with respect to certain instruments compared to strictly manual procedures. For example, robotic-assisted percutaneous access to the kidney in accordance with some procedures can advantageously enable a urologist to perform both direct-entry endoscopic renal access and percutaneous renal access. Although some embodiments of the present disclosure are presented in the context of catheters, nephroscopes, ureteroscopes, and/or human renal anatomy, it should be understood that the principles disclosed herein may be implemented in any type of endoscopic/percutaneous procedure or another type of procedure.

In one illustrative procedure, the medical system 100 can be used to remove a kidney stone 190 from the patient 120. During setup for the procedure, the physician 160 can position the robotic arms 112 of the robotic system 110 in the appropriate/desired configuration. For example, the physician 160 can manually move the first robotic arm 112(A) near a treatment site (i.e., a kidney 191 where the kidney stone 190 is located), as shown in FIG. 1. The EM field generator 140 can be connected to the first robotic arm 112(A) to assist in tracking a location of the scope 130 and/or other instruments during the procedure. Although the first robotic arm 112(A) is positioned relatively close to the patient 120, in some embodiments the first robotic arm 112(A) is positioned elsewhere and/or the EM field generator 140 is integrated into the table 170 (which can allow the first robotic arm 112(A) to be in a docked position).

Further, the physician 160 can manually position the second robotic arm 112(B) between the legs of the patient 120, as shown. In this example, the physician 160 inserts a medical instrument 193 at least partially into the urethra 192 and connects the medical instrument 193 to the second robotic arm 112(B). The medical instrument 193 can include a lumen-type device configured to receive the scope 130 (e.g., an access sheath), thereby assisting in inserting the scope 130 into the anatomy of the patient 120. By aligning the second robotic arm 112(B) to the urethra 192 of the patient 120 and/or using the medical instrument 193, friction and/or forces on the sensitive anatomy in the area can be reduced. Once the medical instrument 193 is inserted at least partially into the urethra 192, the scope 130 can be inserted into the patient 120 manually, robotically, or a combination thereof. Although the medical instrument 193 is illustrated in FIG. 1, in some embodiments, the medical instrument 193 is not used (e.g., the scope 130 is inserted directly into the urethra 192).

The physician 160 can also manually position the third robotic arm 112(C) to align with the second robotic arm 112(B). For example, the third robotic arm 112(C) can be moved to one or more of the alignment positions 180, which can represent alignment to the second robotic arm 112(B). The handle 132 of the scope 130 can then be connected to the distal end of the third robotic arm 112(C). Although this example is discussed in the context of positioning the robotic arms 112 and then connecting the scope 130/EM field generator 140, the scope 130/EM field generator 140 can be connected at any time to the robotic arms 112. For example, the scope 130 can be connected to the third robotic arm 112(C) and then positioned at one or more of the alignment positions 180.

The physician 160 can interact with the control system 150 to cause the robotic system 110 to advance and/or navigate the scope 130 from the urethra 192, through the bladder 194, up the ureter 195, and into the kidney 191. The physician 160 can navigate the scope 130 to locate the kidney stone 190. The control system 150 can provide information via the display(s) 152 regarding the scope 130 to assist the physician 160 in navigating the scope 130. For example, the control system 150 can present an interface (not illustrated) via the display(s) 152 to view a real-time image(s) captured by the scope 130 to assist the physician 160 in controlling the scope 130. In some embodiments, the control system 150 can use localization techniques to determine a position and/or an orientation of the scope 130, which can be viewed by the physician 160 through the display(s) 152 to also assist in controlling the scope 130. Further, in some embodiments, other types of information can be presented through the display(s) 152 to assist the physician 160 in controlling the scope 130, such as x-ray images of the internal anatomy of the patient 120.

Once at the site of the kidney stone 190 (e.g., within a calyx of the kidney 191), the scope 130 can be used to designate/tag a target location for a catheter to access the kidney 191 percutaneously. To minimize damage to the kidney 191 and/or the surrounding anatomy, the physician 160 can designate a papilla, such as a papilla 196, as the target location for entering into the kidney 191 percutaneously. However, other target locations can be designated or determined. In some embodiments of designating the papilla 196, the physician 160 can navigate the scope 130 to contact the papilla 196, the control system 150 can use localization techniques to determine a location of the scope 130 (e.g., a location of the end of the scope 130), and the control system 150 can associate the location of the scope 130 with the target location. Further, in some embodiments, the physician 160 can navigate the scope 130 to be within a particular distance to the papilla 196 (e.g., park in front of the papilla 196) and provide input indicating that the target location is within a field-of-view of the scope 130. The control system 150 can perform image analysis and/or other localization techniques to determine a location of the target location. Moreover, in some embodiments, the scope 130 can deliver a fiduciary to mark the papilla 196 as the target location.

When the target location is designated, the physician 160 can remove the EM field generator 140 from the first robotic arm 112(A) and attach a catheter to the first robotic arm 112(A). The physician 160 can interact with the control system 150 to cause the robotic system 110 to advance and/or navigate the catheter to the target location through a percutaneous access path in the patient 120 (e.g., through the skin of the patient 120 and into the kidney 120 via the designated papilla 196). In some embodiments, a needle or another medical instrument is inserted into the patient 120 to create the percutaneous access path and the catheter is then inserted therein. The catheter can be controlled by the first robotic arm 112(A), such as to insert, retract, and/or articulate the catheter to reach the target site and/or to remove the kidney stone 190 from the patient 120. The control system 150 can provide information via the display(s) 152 regarding the catheter to assist the physician 160 in navigating the catheter. For example, an interface(s) can provide image data from the perspective of the scope 130. The image data may depict the catheter (e.g., when within the field-of-view of an imaging device of the scope 130), so that the catheter can be navigated/controlled in the appropriate manner.

With the scope 130 and/or the catheter located at the target location (e.g., via different access paths), the physician 160 can use the scope 130 to break up the kidney stone 190 and/or use the catheter to extract pieces of the kidney stone 190 from the patient 120. For example, the scope 130 can deploy a tool (e.g., a laser, a cutting instrument, etc.) to fragment the kidney stone 190 into pieces and the catheter can suck out the pieces from the kidney 191 through the percutaneous access path. In examples, the catheter and/or the scope 130 can provide irrigation and/or aspiration to facilitate removal of the kidney stone 190. For instance, the catheter can be coupled to an irrigation and/or aspiration system (not illustrated). As noted above, the control system 150 can provide image data from the perspective of the scope 130 to assist in removing the kidney stone 190 (e.g., view that the kidney stone 190 is being broken up and removed from the kidney 191 using the catheter).

At any point before, during, or after the procedure, the medical system 100 can implement the alignment techniques discussed herein to position one or more of the robotic arms 112. In one example, when the third robotic arm 112(C) is being aligned with the second robotic arm 112(B) (e.g., to the alignment positions 180), the third robotic arm 112(C) can exhibit different amounts of resistance to indicate to the physician 160 if the third robotic arm 112(C) is moving closer or farther from the alignment positions 180. In another example, the robotic system 110/control system 150 can store information indicating a location of the distal end of the first robotic arm 112(A) as illustrated in FIG. 1. The physician 160 can then place the first robotic arm 112(A) to the side away from the patient 120 to detach the EM field generator 140 (e.g., once the scope 130 has reached the target site) and attach a catheter or another instrument. The first robotic arm 112(A) can be arranged for use of the catheter. Once the catheter has been used, the physician 160 can reattach the EM field generator 140 by moving the first robotic arm 112(A) to the side again. The physician 160 can provide input indicating that the EM field generator 140 is attached again and requesting realignment with the previous position of the first robotic arm 112(A). The first robotic arm 112(A) can exhibit different amounts of resistance to indicate to if the first robotic arm 112(A) is moving closer or farther from the previous position of the first robotic arm 112(A).

The medical system 100 can provide a variety of benefits, such as providing guidance to assist a physician in performing a procedure (e.g., instrument tracking, instrument navigation, instrument calibration, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between at least the control system 150 and the robotic system 110, which can be independently movable. Such distribution of functionality and/or mobility can enable the control system 150 and/or the robotic system 110 to be placed at locations that are optimal for a particular medical procedure, which can maximize working area around the patient and/or provide an optimized location for a physician to perform a procedure.

Although various techniques and systems are discussed as being implemented as robotically-assisted procedures (e.g., procedures that at least partly use the medical system 100), the techniques and systems can be implemented in other procedures, such as in fully-robotic medical procedures, human-only procedures (e.g., free of robotic systems), and so on. For example, the medical system 100 can be used to perform a procedure without a physician holding/manipulating a medical instrument (e.g., a fully-robotic procedure).

That is, medical instruments that are used during a procedure can each be held/controlled by components of the medical system 100, such as the robotic arms 112 of the robotic system 110.

Example Control System and Robotic System

Figure 2:
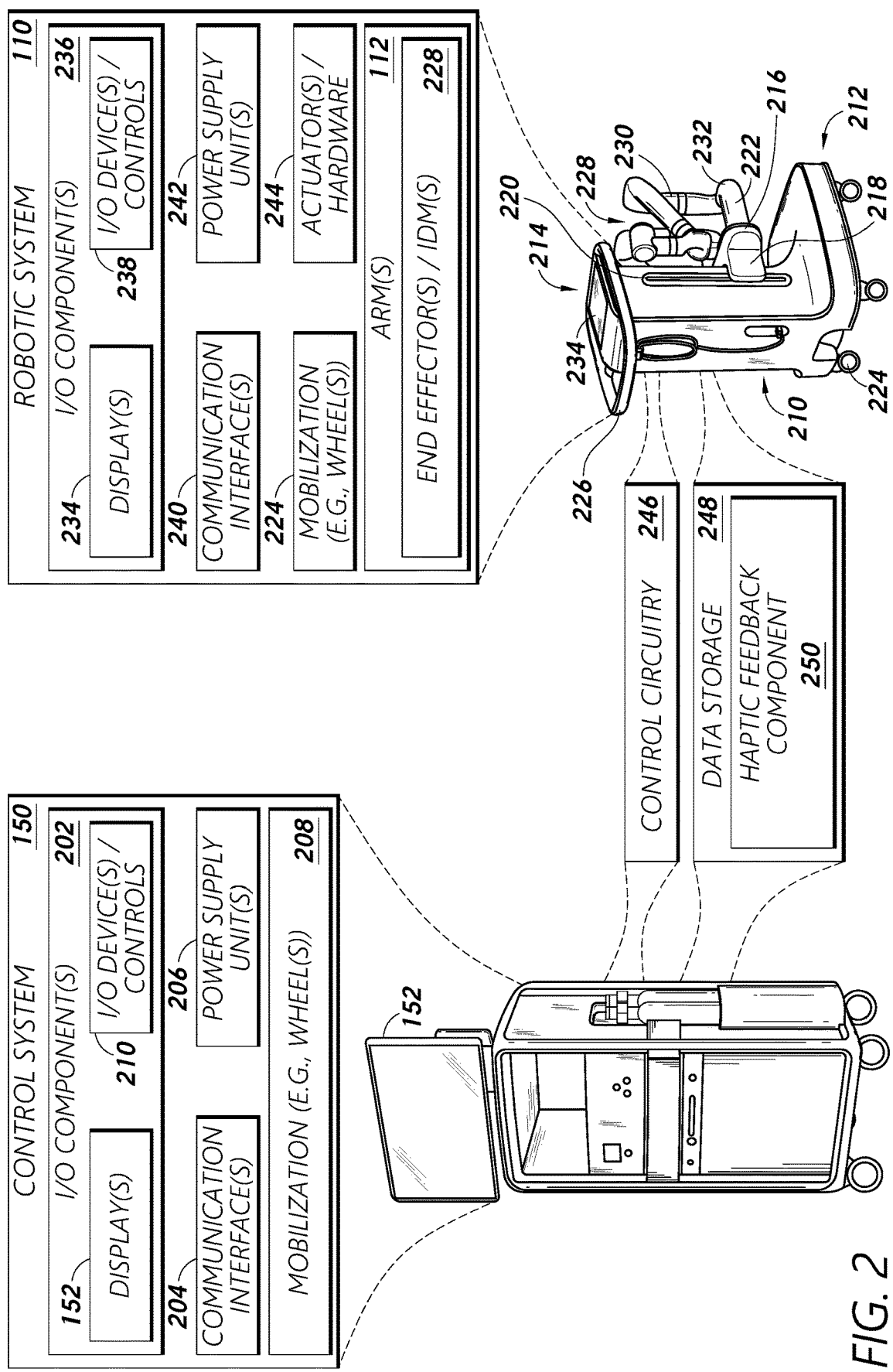
FIG. 2 illustrates example details of the control system and the robotic system of FIG. 1 in accordance with one or more embodiments.
Figure 3:
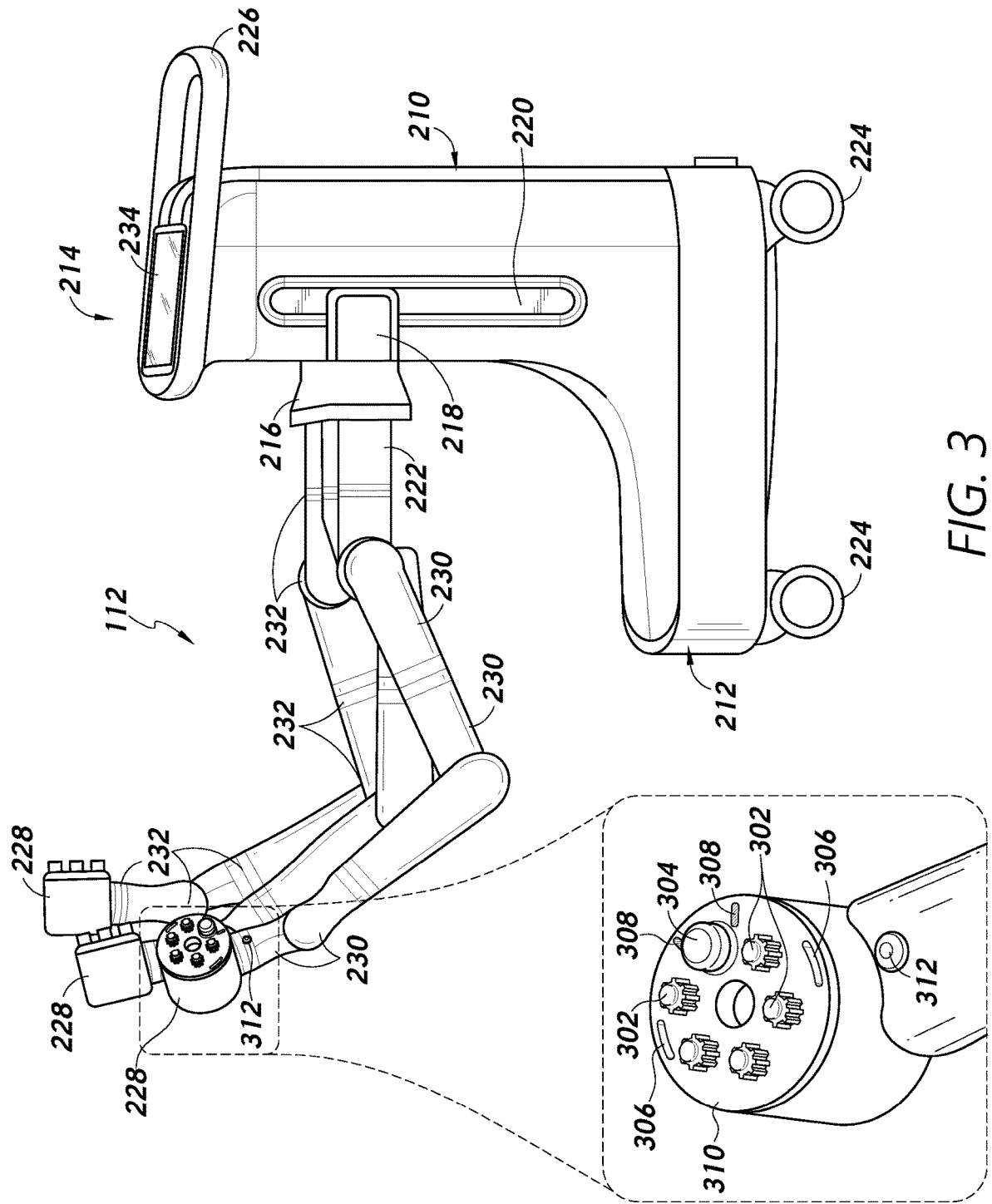
FIG. 3 illustrates example details of the robotic system of FIG. 1 in accordance with one or more embodiments.

FIG. 2 shows example details of the control system 150 and the robotic system 110 of FIG. 1, while FIG. 3 shows additional details of the robotic system 110 in accordance with one or more embodiments. Although certain components of the control system 150 and/or the robotic system 110 are illustrated in FIGS. 2 and/or 3, it should be understood that additional components not shown can be included in embodiments in accordance with the present disclosure. Furthermore, any of the illustrated components can be omitted, interchanged, and/or integrated into other devices/systems, such as the table 170, a medical instrument, etc.

With reference to FIG. 2, the control system 150 can include one or more of the following components, devices, modules, and/or units (referred to herein as "components"), either separately/individually and/or in combination/collectively: one or more I/O components 202, one or more communication interfaces 204, one or more power supply units 206, and/or one or more mobilization components 208 (e.g., casters or other types of wheels). In some embodiments, the control system 150 can comprise a housing/enclosure configured and/or dimensioned to house or contain at least part of one or more of the components of the control system 150. In this example, the control system 150 is illustrated as a cart-based system that is movable with the one or more mobilization components 208. In some cases, after reaching the appropriate position, the one or more mobilization components 208 can be immobilized using wheel locks to hold the control system 150 in place. However, the control system 150 can be implemented as a stationary system, integrated into another system/device, and so on.

The various components of the control system 150 can be electrically and/or communicatively coupled using certain connectivity circuitry/devices/features, which may or may not be part of control circuitry. For example, the connectivity feature(s) can include one or more printed circuit boards configured to facilitate mounting and/or interconnectivity of at least some of the various components/circuitry of the control system 150. In some embodiments, two or more of the components of the control system 150 can be electrically and/or communicatively coupled to each other.

The one or more I/O components/devices 202 can include a variety of components to receive input and/or provide output, such as to interface with a user to assist in performing a medical procedure. The one or more I/O components 202 can be configured to receive touch, speech, gesture, or any other type of input. In examples, the one or more I/O components 202 can be used to provide input regarding control of a device/system, such as to control the robotic system 110, navigate a scope or other medical instrument attached to the robotic system 110, control the table 170, control a fluoroscopy device, and so on. For example, the physician 160 (not illustrated) can provide input via the I/O component(s) 202 and, in response, the control system 150 can send control signals to the robotic system 110 to manipulate a medical instrument. In examples, the physician 160 can use the same I/O device to control multiple medical instruments (e.g., switch control between the instruments).

As shown, the one or more I/O components 202 can include the one or more displays 152 (sometimes referred to as "the one or more display devices 152") configured to display data. The one or more displays 152 can include one or more liquid-crystal displays (LCD), light-emitting diode (LED) displays, organic LED displays, plasma displays, electronic paper displays, and/or any other type(s) of technology. In some embodiments, the one or more displays 152 include one or more touchscreens configured to receive input and/or display data. Further, the one or more I/O components 202 can include one or more I/O devices/controls 210, which can include a touch pad, controller (e.g., hand-held controller, video-game-type controller, etc.), mouse, keyboard, wearable device (e.g., optical head-mounted display), virtual or augmented reality device (e.g., head-mounted display), etc. Additionally, the one or more I/O components 202 can include one or more speakers configured to output sounds based on audio signals and/or one or more microphones configured to receive sounds and generate audio signals. In some embodiments, the one or more I/O components 202 include or are implemented as a console.

In some embodiments, the one or more I/O components 202 can output information related to a procedure. For example, the control system 150 can receive real-time images that are captured by a scope and display the real-time images and/or visual representations of the real-time images via the display(s) 152. The display(s) 152 can present an interface(s), such as any of the interfaces discussed herein, which can include image data from the scope and/or another medical instrument. Additionally, or alternatively, the control system 150 can receive signals (e.g., analog, digital, electrical, acoustic/sonic, pneumatic, tactile, hydraulic, etc.) from a medical monitor and/or a sensor associated with a patient, and the display(s) 152 can present information regarding the health or environment of the patient. Such information can include information that is displayed via a medical monitor including, for example, a heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEC), environmental and/or local or core body temperature, and so on.

The one or more communication interfaces 204 can be configured to communicate with one or more device/sensors/systems. For example, the one or more communication interfaces 204 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 204 can implement a wireless technology, such as Bluetooth, Wi-Fi, near field communication (NFC), or the like.

The one or more power supply units 206 can be configured to manage and/or provide power for the control system 150 (and/or the robotic system 110, in some cases). In some embodiments, the one or more power supply units 206 include one or more batteries, such as a lithium-based battery, a lead-acid battery, an alkaline battery, and/or another type of battery. That is, the one or more power supply units 206 can comprise one or more devices and/or circuitry configured to provide a source of power and/or provide power management functionality. Moreover, in some embodiments the one or more power supply units 206 include a mains power connector that is configured to couple to an alternating current (AC) or direct current (DC) mains power source.

Although not shown in FIG. 2, the control system 150 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 150 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

In some embodiments, the control system 150 can include support equipment for sensors deployed throughout the medical system 100. For example, the control system 150 can include opto-electronics equipment for detecting, receiving, and/or processing data received from optical sensors and/or cameras. Such opto-electronics equipment can be used to generate real-time images for display in any number of devices/systems, including in the control system 150. Similarly, the control system 150 can include an electronic subsystem for receiving and/or processing signals received from deployed electromagnetic (EM) sensors. In some embodiments, the control system 150 can also be used to house and/or position an EM field generator for detection by EM sensors in or on a medical instrument.

Further, in some embodiments, the control system 150 can be coupled to the robotic system 110, the table 170, and/or a medical instrument, through one or more cables or connections (not shown). In some implementations, support functionality from the control system 150 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

With reference to FIGS. 2 and 3, the robotic system 110 generally includes an elongated support structure 210 (also referred to as a "column"), a robotic system base 212, and a console 214 at the top of the column 210. The column 210 can include one or more carriages 216 (also referred to as "the arm support 216") for supporting the deployment of one or more the robotic arms 112. The carriage 216 can include individually configurable arm mounts that rotate along a perpendicular axis to adjust the base of the robotic arms 112 for positioning relative to a patient. The carriage 216 also includes a carriage interface 218 that allows the carriage 216 to vertically translate along the column 210. The carriage interface 218 can be connected to the column 210 through slots, such as slot 220, that are positioned on opposite sides of the column 210 to guide the vertical translation of the carriage 216. The slot 220 can include a vertical translation interface to position and/or hold the carriage 216 at various vertical heights relative to the base 212. Vertical translation of the carriage 216 allows the robotic system 110 to adjust the reach of the robotic arms 112 to meet a variety of table heights, patient sizes, physician preferences. etc. Similarly, the individually configurable arm mounts on the carriage 216 allow a robotic arm base 222 of the robotic arms 112 to be angled in a variety of configurations. The column 210 can internally comprise mechanisms, such as gears and/or motors, that are designed to use a vertically aligned lead screw to translate the carriage 216 in a mechanized fashion in response to control signals generated in response to user inputs, such as inputs from an I/O device(s).

The base 212 can balance the weight of the column 210, the carriage 216, and/or robotic arms 112 over a surface, such as the floor. Accordingly, the base 212 can house heavier components, such as one or more electronics, motors, power supply, etc., as well as components that enable movement and/or immobilize the robotic system 110. For example, the base 212 can include rollable wheels 224 (also referred to as "the casters 224" or "the mobilization components 224") that allow for the robotic system 110 to move around the room for a procedure. After reaching an appropriate position, the casters 224 can be immobilized using wheel locks to hold the robotic system 110 in place during the procedure. As shown, the robotic system 110 also includes a handle 226 to assist with maneuvering and/or stabilizing the robotic system 110. In this example, the robotic system 110 is illustrated as a cart-based system that is movable. However, the robotic system 110 can be implemented as a stationary system, integrated into a table, and so on.

The robotic arms 112 can generally comprise robotic the arm bases 222 and end effectors 228, separated by a series of linkages 230 (also referred to as "arm segments 230") that are connected by a series of joints 232. Each joint 232 can comprise an independent actuator and each actuator can comprise an independently controllable motor. Each independently controllable joint 232 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 228 at a specific position, orientation, and/or trajectory in space using different linkage positions and/or joint angles. In some embodiments, the end effectors 228 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

The end effector 228 of each of the robotic arms 112 can comprise an instrument device manipulator (IDM), which may be referred to as or attached using a mechanism changer interface (MCI). In some embodiments, the same IDM can be used to attach different instruments/devices, such as a scope, catheter, EM field generator, etc. In other embodiments, the IDM can be removed and replaced with a different type of IDM for different types of instruments/devices. For example, a first type of IDM can manipulate an endoscope, a second type of IDM can manipulate a catheter, a third type of IDM can hold an EM field generator, and so on. An IDM/MCI can include connectors to transfer pneumatic pressure, electrical power, electrical signals, and/or optical signals with the robotic arm 112. The IDMs 228 and/or medical instruments (e.g., surgical tools/instruments) can include direct drives, harmonic drives, geared drives, belts and pulleys, magnetic drives, and the like. In some embodiments, the IDMs 228 can be attached to respective ones of the robotic arms 112, wherein the robotic arms 112 are configured to insert or retract the respective coupled medical instruments into or out of the treatment site.

The end effector 228 of each of the robotic arms 112 can include various components/elements to connect to and/or align with a medical instrument. As shown in the enlarged image of the end effector 228 of one of the robotic arms 112, the end effector 228 can include multiple gears 302 to control/articulate a medical instrument, a reader 304 to read data from a medical instrument (e.g., radio-frequency identification (RFID) reader to read a serial number from a medical instrument), fasteners 306 to attach a medical instrument to the IDM 228 (e.g., latches to secure the medical instrument), markers 308 to align with an instrument that is manually attached to a patient (e.g., an access sheath) and/or to define a front surface of the IDM 228. In some embodiments, a portion 310 of the end effector 228 (e.g., plate) can be configured to rotate/spin, such as by a user when the robotic arm 112 is operating in the admittance control mode.

An end effector 228 can be configured to couple directly to a medical instrument and/or to the medical instrument via another device. For example, an adapter (not illustrated) can be removably and/or detachably coupled to the end effector 228 to provide an interface (e.g., driver interface) between the end effector 228 and the medical instrument. The adapter can include connectors to transfer pneumatic pressure, electrical power, electrical signals, and/or optical signals. In some embodiments, the adapter may be devoid of any electro-mechanical components, such as motors. Additionally, or alternatively, in some configurations, a sterile drape, such as a plastic sheet or the like, may be disposed between the end effector 228 and a medical instrument/adapter to provide a sterile barrier between the robotic arm 112 and the medical instrument. The adapter and/or sterile drape may be implemented due to the need to sterilize medical instruments used in medical procedures and/or the inability to adequately sterilize expensive capital equipment due to their intricate mechanical assemblies and/or sensitive electronics. Accordingly, a medical instrument, adapter, and/or sterile drape may be designed to be detached, removed, and/or interchanged from a robotic arm 112 for individual sterilization or disposal. In contrast, the robotic arm 112 need not be changed or sterilized in some cases and/or may be draped for protection. Components like the adapter may be referred to as a mechanism changer interfaces (MCI) in some contexts.

In some embodiments, the robotic arms 112 can be configured to control a position, orientation, and/or tip articulation of a medical instrument (e.g., a sheath and/or a leader of a scope) attached thereto. For example, the robotic arms 112 can be configured/configurable to manipulate a scope using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope to deflect the tip of the scope. Pull wires can include any suitable or desirable materials, such as metallic and/or non-metallic materials such as stainless steel, Kevlar, tungsten, carbon fiber, and the like. In some embodiments, the scope is configured to exhibit nonlinear behavior in response to forces applied by the elongate movement members. The nonlinear behavior can be based on stiffness and compressibility of the scope, as well as variability in slack or stiffness between different elongate movement members.

As shown, the console 214 is positioned at the upper end of column 210 of the robotic system 110. The console 214 can include a display(s) 234 to provide a user interface for receiving user input and/or providing output (e.g., a dual-purpose device, such as a touchscreen) to provide a physician/user with pre-operative data, intra-operative data, information to configure the robotic system 110, and so on. Potential pre-operative data can include pre-operative plans, navigation and mapping data derived from pre-operative computerized tomography (CT) scans, and/or notes from pre-operative patient interviews. Intra-operative data can include optical information provided from a tool, sensor and/or coordinate information from sensors, as well as vital patient statistics, such as respiration, heart rate, and/or pulse. The console 214 can be positioned and tilted to allow a physician to access the console 214 from the side of the column 214 opposite arm support 216. From this position, the physician may view the console 214, robotic arms 112, and patient while operating the console 214 from behind the robotic system 110.

The robotic system 110 can include one or more I/O components/devices 236 to receive input and/or provide output, such as to interface with a user. The one or more I/O components 236 can be configured to receive touch, speech, gesture, or any other type of input. In examples, the one or more I/O components 236 can be used to provide input regarding control of a device/system, such as to control/configure the robotic system 110. As shown, the one or more I/O components 236 can include the one or more displays 234 configured to display data. The one or more displays 234 can include one or more liquid-crystal displays (LCD), light-emitting diode (LED) displays, organic LED displays, plasma displays, electronic paper displays, and/or any other type(s) of technology. In some embodiments, the one or more displays 234 include one or more touchscreens configured to receive input and/or display data. Further, the one or more I/O components 236 can include one or more I/O devices/controls 238, which can include a touch pad, controller, mouse, keyboard, wearable device (e.g., optical head-mounted display), virtual or augmented reality device (e.g., head-mounted display), etc. Additionally, the one or more I/O components 236 can include one or more speakers configured to output sounds based on audio signals and/or one or more microphones configured to receive sounds and generate audio signals. In some embodiments, the one or more I/O components 236 include or are implemented as the console 214. Further, the one or more I/O components 236 can include one or more buttons that can be physically pressed, such as a button 312 on a distal end of a robotic arm 112 (which can enable/disable an admittance control mode).

The various components of the robotic system 110 can be electrically and/or communicatively coupled using certain connectivity circuitry/devices/features, which may or may not be part of control circuitry. For example, the connectivity feature(s) can include one or more printed circuit boards configured to facilitate mounting and/or interconnectivity of at least some of the various components/circuitry of the robotic system 110. In some embodiments, two or more of the components of the robotic system 110 can be electrically and/or communicatively coupled to each other.

In some embodiments, one or more of the robotic arms 112 and/or the robotic system 110 can be configured to operate an admittance control mode. As used herein, the term "admittance control mode" (or simply "admittance mode") can refer to a control mode of a robotic arm 112/robotic system 110 in which the user controls the movement of the robotic arm 112 by applying forces thereto. For example, when operating in the admittance control mode, a robotic arm 112 can be manually moved by a user without using electronic user controls, such as by grasping the robotic arm 112 and applying a force thereto. As such, the user may be able to directly control the position of the robotic arm. In examples, a robotic arm 112 can include a driving component(s) configured to reposition and/or maintain the current pose (e.g., orientation and position) of the robotic arm 112 (e.g., motor/actuator to control movement of the robotic arm 112). Thus, in order to provide admittance control functionality, the robotic system 110/control system 150 can measure the force imparted to the robotic arm 112 by the user and actuate one or more of the driving components using the measured force as an input value.

To illustrate, when the admittance control mode is enabled, a robotic arm 112 can be freely moved by the user with manual manipulation of the robotic arm 112 based on a force applied to the robotic arm. For example, the user can grab the distal end of the robotic arm 112 and apply a force to position the distal end of the robotic arm 112 (and/or other portions of the robotic arm 112) at a desired position. When the admittance control mode is disabled and/or a force applied to the robotic arm is less than a threshold, the robotic arm 112 can remain fixed to a position (e.g., inhibit manual movement of the robotic arm 112). In some cases, in the admittance control mode, the robotic arm 112 can be moved in a X, Y, Z manner without changing an orientation of an end effector of the robotic arm 112 (e.g., a user cannot tilt the robotic arm 112). However, in other embodiments, the orientation of the third robotic arm 112(C) can be changed in the admittance control mode.

The robotic arms 112/robotic system 110 can enter/exit the admittance control mode in a variety of manners. For example, a user can provide input via the robotic system 110/control system 150 (e.g., an interface, controller, etc.), provide input via the button 312 on a robotic arm 112, or otherwise provide input to enable/disable an admittance control mode. In some embodiments, an end effector 228 and/or arm segment 230 of a robotic arm 112 includes one or more buttons, such as the button 312 (also referred to as "the admittance control button 312"), that when actuated/contacted enables the admittance control mode (e.g., transitions the robotic arm 112 to the admittance control mode). In the example of FIG. 3, the button 312 is illustrated on the arm segment 230 in proximity to the end effector 228 (e.g., within a particular distance). However, the button 312 can be located at other locations, such as on the end effector 228, a joint, or elsewhere. In many embodiments, each distal arm segment 230/end effector 228 of a robotic arm 112 can include a button to enable/disable the admittance control mode for the respective arm 112. However, in some embodiments, a single input can enable/disable the admittance control mode for multiple robotic arms 112. Although the admittance control mode is discussed in many examples as being enabled/disabled in the context of pressing the button 312, the admittance control mode can be enabled/disabled in a variety of manners, such as through any type of I/O device.

The robotic arms 112 can generally exhibit some amount of resistance when operating in the admittance control mode. The amount of resistance can affect the amount of force needed to move the robotic arm 112, to move the robotic arm 112 at a particular velocity, to move the robotic arm 112 a particular distance, etc. As such, an amount of resistance associated with manual movement of a robotic arm 112 can be indicative of a force exerted back to the user when manually moving the robotic arm 112. In some embodiments, one or more actuators/hardware 244 of a robotic arm 112 can be controlled to configure an amount of resistance for manual movement of the robotic arm 112. For example, a motor in a joint of a robotic arm 112 can be controlled based on a resistance parameter/value such that the robotic arm 112 exhibits a particular amount of resistance when the robotic arm 112 is moved by a user. In some embodiments, when operating in the admittance control mode, one or more parameters can be used to determine a speed to move the robotic arm 112, such as a force applied by a user on the robotic arm 112, virtual mass of the robotic arm 112, and/or virtual damping. The virtual mass can indicate how heavy the robotic arm 112 feels by the user (e.g., acceleration of robot motion), while virtual damping can provide a resistance feel to the user (e.g., how fast the robotic arm 112 moves).

In some embodiments, an amount of resistance associated with manual movement of a robotic arm 112 can be based on a direction of movement of the robotic arm 112 and/or a proximity of the robotic arm 112 relative to a particular position. For example, the control system 150/robotic system 110 can configure the robotic arm 112 to provide a first amount of resistance for manual movement in a direction closer to an alignment position and configure the robotic arm 112 to provide a second amount of resistance for manual movement in a direction away from an alignment position. Further, when an alignment position is reached, the control system 150/robotic system 110 can configure the robotic arm 112 to provide a third amount of resistance for manual movement between alignment positions and/or to provide a fourth amount of resistance for manual movement away from the alignment position.

The one or more communication interfaces 240 can be configured to communicate with one or more device/sensors/systems. For example, the one or more communication interfaces 240 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 240 can implement a wireless technology such as Bluetooth, Wi-Fi, near field communication (NFC), or the like.

The one or more power supply units 242 can be configured to manage and/or provide power for the robotic system 110. In some embodiments, the one or more power supply units 242 include one or more batteries, such as a lithium-based battery, a lead-acid battery, an alkaline battery, and/or another type of battery. That is, the one or more power supply units 242 can comprise one or more devices and/or circuitry configured to provide a source of power and/or provide power management functionality. Moreover, in some embodiments the one or more power supply units 242 include a mains power connector that is configured to couple to an alternating current (AC) or direct current (DC) mains power source.

The robotic system 110 can also include the one or more actuators/hardware 244 to facilitate movement of the robotic arms 112. Each actuator 244 can comprise a motor, which can be implemented in a joint or elsewhere within a robotic arm 112 to facilitate movement of the joint and/or a connected arm segment/linkage. Further, the robotic system 110 can include a variety of other components, such as pneumatics, optical sources, etc.

With reference to FIG. 2, the control system 150 and/or the robotic system 110 can include control circuitry 246 and/or data storage/memory 248 configured to perform functionality described herein. For ease of discussion and illustration, the control circuitry 246 and data storage 248 are shown in blocks between the control system 150 and the robotic system 110. It should be understood that, in many embodiments, the control system 150 and the robotic system 110 can include separate instances of the control circuitry 246 and the data storage 248. That is, the control system 150 can include its own control circuitry and data storage (e.g., to implement processing on the control system 150), while the robotic system 110 can include its own control circuitry and data storage (e.g., to implement processing on the robotic system 110). In many embodiments, reference to control circuitry may refer to circuitry embodied in a robotic system, a control system, or any other component of a medical system, such as any component of the medical system 100 shown in FIG. 1.

Although the control circuitry 246 is illustrated as a separate component from other components of the control system 150/robotic system 110, it should be understood that any or all of the other components of the control system 150 and/or the robotic system 110 can be embodied at least in part in the control circuitry 246. For instance, the control circuitry 246 can include various devices (active and/or passive), semiconductor materials and/or areas, layers, regions, and/or portions thereof, conductors, leads, vias, connections, and/or the like, wherein one or more of the other components of the control system 150/robotic system 110 and/or portion(s) thereof can be formed and/or embodied at least in part in/by such circuitry components/devices.

As illustrated, the data storage 248 can include a haptic feedback component 250 configured to facilitate various functionality discussed herein. For example, the haptic feedback component 250 can be configured to determine an alignment position(s) for a robotic arm 112, determine a direction/proximity of the robotic arm 112 relative to the alignment position(s), set a resistance for manual movement of the robotic arm 112, control the robotic arm 112 to automatically move (e.g., when within proximity to an alignment position), and so on. In some embodiments, the haptic feedback component 250 can include one or more instructions that are executable by the control circuitry 246 to perform one or more operations. Although many embodiments are discussed in the context of the haptic feedback component 250 implemented as (or including) one or more instructions that are executable by the control circuitry 246, the haptic feedback component 250 (and/or other components, such as a localization component) can be implemented at least in part as control circuitry.

Although not illustrated in FIG. 3, in some embodiments the data storage 248 includes a localization component configured to perform one or more localization techniques to determine and/or track a position and/or an orientation of an object, such as a medical instrument connected to the robotic system 110. For example, the localization component can process input data, such as sensor data from a medical instrument (e.g., EM field sensor data, vision data captured by an imaging device/depth sensor on the medical instrument, accelerometer data from an accelerometer on the medical instrument, gyroscope data from a gyroscope on the medical instrument, satellite-based positioning data from a satellite-based sensor (a global positioning system (GPS), for example), and so on), robotic command and/or kinematics data for the robotic arms 112, sensor data from a shape sensing fiber (e.g., which can provide shape data regarding a location/shape of the medical instrument), model data regarding anatomy of a patient, position data of a patient, pre-operative data, etc. Based on such processing, the localization component can generate position/orientation data for a medical instrument. The position/orientation data can indicate a location and/or an orientation of the medical instrument relative to a frame of reference. The frame of reference can be a frame of reference relative to anatomy of a patient, a known object (e.g., an EM field generator), a coordinate system/space, and so on. In some implementations, position/orientation data can indicate a location and/or an orientation of a distal end of a medical instrument (and/or proximal end, in some cases). A position and orientation of an object can be referred to as a pose of the object.

In some implementations, the localization component can use electromagnetic tracking to determine a position and/or an orientation of an object. For example, the localization component can use real-time EM tracking to determine a real-time location of a medical instrument in a coordinate system/space that can be registered to the patient's anatomy, which can be represented by a pre-operative model or other model. In EM tracking, an EM sensor (or tracker) including one or more sensor coils can be embedded in one or more locations and/or orientations in a medical instrument (e.g., a scope, a needle, etc.). The EM sensor can measure a variation in an EM field created by one or more static EM field generators positioned at a known location. The location information detected by the EM sensors can be stored as EM data. The localization component can process the EM data to determine a position and/or orientation of an object, such as a medical instrument. An EM field generator (or transmitter) can be placed close to the patient (e.g., within a predetermined distance) to create a low intensity magnetic field that an EM sensor can detect. The magnetic field can induce small currents in the sensor coils of the EM sensor, which can be analyzed to determine a distance and/or angle between the EM sensor and the EM field generator. These distances and/or orientations can be intra-operatively "registered" to patient anatomy (e.g., a pre-operative model) in order to determine a geometric transformation that aligns a single location in a coordinate system with a position in the pre-operative model of the patient's anatomy. Once registered, an EM sensor (e.g., an embedded EM tracker) in one or more positions of a medical instrument (e.g., the distal tip of an endoscope, a needle, etc.) can provide real-time indications of a position and/or an orientation the medical instrument through the patient's anatomy.

Although various techniques are discussed in the context of providing haptic feedback to assist in aligning a robotic arm, other techniques can additionally, or alternatively, be implemented to facilitate such alignment. In some embodiments, the control system 150 and/or the robotic system 110 can display information to assist in aligning a robotic arm relative to a desired alignment position, such as a position of the robotic arm relative to an alignment position, a distance of the robotic arm to the alignment position, a visual representation of the alignment position, a visual representation of a virtual rail, a visual representation of a robotic arm, and so on. In some cases, the user can manually move the robotic arm to an initial position in proximity to an alignment position, and then use an I/O device to finalize alignment to a desired location (e.g., control fine adjustments). In other cases, the user can use the I/O device without any manual manipulation. In any case, the robotic system 110 and/or the control system 150 can display the information noted above. Further, in some embodiments, a robotic arm can be automatically moved to an alignment position without any user input/user manipulation of the robotic arm. For example, a user can position a first robotic arm and then select a button via an I/O device to instruct the robotic system 110 to align a second robotic arm with the first robotic arm. Moreover, in some embodiments, multiple robotic arms can be correlated so that movement of one robotic arm causes another robotic arm to be automatically moved. For example, as a user positions a first robotic arm (e.g., manually or using electronic controls), a second robotic arm can move in a correlated manner. Furthermore, in some embodiments, when two or more robotic arms are initially aligned, the two or more robotic arms can move together in a correlated manner (e.g., the two or more robotic arms can move simultaneously in the same direction as one of the arms is controlled to move).

Further, although various techniques implement resistive feedback to assist in aligning a robotic arm, other types of feedback can be implemented. For example, a robotic arm can provide different types of vibration (with the robotic arm including a vibrator to generate the vibrations) to indicate if the robotic arm is moving closer/farther from an alignment position and/or to indicate a proximity of the robotic arm to an alignment position. Alternatively, or additionally, the robotic system 110 and/or the control system 150 can output different sounds to indicate if the robotic arm is moving closer/farther from an alignment position and/or to indicate a proximity of the robotic arm to an alignment position.

The term "control circuitry" is used herein according to its broad and ordinary meaning, and can refer to any collection of one or more processors, processing circuitry, processing modules/units, chips, dies (e.g., semiconductor dies including one or more active and/or passive devices and/or connectivity circuitry), microprocessors, micro-controllers, digital signal processors, microcomputers, central processing units, graphics processing units, field programmable gate arrays, application specific integrated circuits, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Example Haptic-Assisted Robotic Arm Positioning

FIGS. 4-9 illustrate a top view of certain devices/components of the medical system 100 of FIG. 1, with the robotic system 110 configured to provide haptic feedback for one or more of the robotic arms 112 in accordance with one or more embodiments. In these examples, the medical system 100 is arranged in an operating room to remove a kidney stone from the patient 120. In many embodiments, the patient 120 is positioned in a modified supine position with the patient 120 slightly tilted to the side to access the back or side of the patient 120. However, the patient 120 can be positioned in other manners, such as a supine position, a prone position, and so on. For ease of illustration, a portion of the right leg of the patient 120 and a portion of the table 170 is not shown. Although FIGS. 4-9 illustrate use of the medical system 100 to remove a kidney stone from the patient 120, the medical system 100 can be used to perform other procedures and/or to remove a kidney stone in other manners. Further, although various acts are illustrated as being performed by the physician 160 in a particular manner, such as with the physician 160 positioned at a particular location, a particular hand of the physician 160 performing an act, and so on, the acts can be performed in a variety of manners. FIGS. 4-9 illustrate an example of aligning the third robotic arm 112(C) with a second robotic arm 112(B) during a setup phase of a procedure. However, it should be understood that the alignment techniques can be implemented in other contexts.

Figure 4:
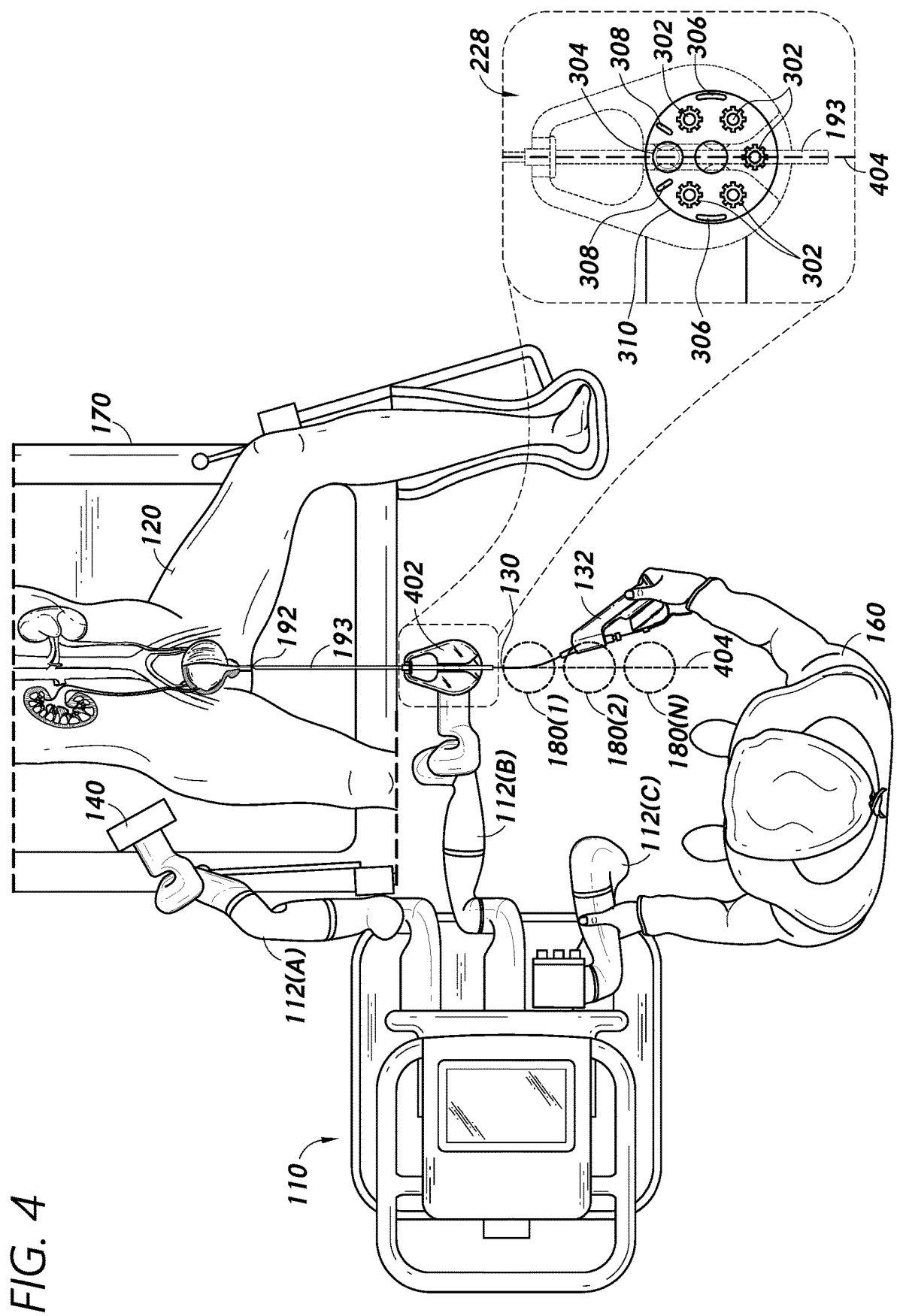
FIG. 4 illustrates example alignment positions for a robotic arm in accordance with one or more embodiments.

As shown in FIG. 4, the physician 160 can position the robotic system 110 at the desired position for the procedure. The physician 160 can then enable the admittance control mode for the first robotic arm 112(A) and manually position the first robotic arm 112(A) near a treatment site. The physician 160 can connect the EM field generator 140 to the end effector of the first robotic arm 112(A). The EM field generator 140 can facilitate localization techniques (e.g., tracking a position of a device/instrument). The physician 160 can also enable the admittance control mode for the second robotic arm 112(B) and manually position the second robotic arm 112(B) between the legs of the patient 120 to align with anatomy of the patient 120, such as the urethra 192 of the patient 120. The physician 160 can connect a scope-driver instrument coupling 402 to the end effector of the second robotic arm 112(B). The scope-driver instrument coupling 402 can facilitate robotic control/advancement of the scope 130. The physician 160 can insert the medical instrument 193 (e.g., access sheath) at least partially into the urethra 192 of the patient 120 and connect the medical instrument 193 to the scope-driver instrument coupling 402. The physician 160 can then insert the scope 130 into the patient 120. That is, the scope 130 can be inserted into the medical instrument 193 and advanced into the patient 120 via the medical instrument 193.

To facilitate alignment of the third robotic arm 112(C) to the second robotic arm 112(B), the robotic system 110 and/or the control system 150 (not illustrated) can determine a virtual rail 404. The virtual rail 404 can represent a line/axis that extends through a center of the end effector 228 of the second robotic arm 112(B), as illustrated in FIG. 4. An angle of the virtual rail 404 through the end effector 228 can be based on an orientation of an element on the end effector 228 of the second robotic arm 112(B), such as one or more of the elements 302-310 described above in reference to FIG. 3. Such elements 302-310 can be disposed on a rotatable plate 310 on the end effector 228 of the second robotic arm 112(B). The physician 160 can rotate/spin the plate 310 of the second robotic arm 112(B) to a specific orientation so that the scope-driver instrument coupling 402 can be attached with a specific orientation. For example, the markers 308 can be aligned so that the medical instrument 193 can be attached to the scope-driver instrument coupling 402 with the medical instrument 193 aligned to the urethra 192 of the patient 120. In this example, the robotic system 110 and/or the control system 150 defines the virtual rail 404 to pass through the reader 304 and the center of the end effector 228 of the second robotic arm 112(B), as shown in FIG. 4. Here, the virtual rail 404 represents an axis/line that is coaxially aligned with the medical instrument 193 (e.g., access sheath for the scope 130). However, the virtual rail 404 can pass through a variety of components/reference points.

Based on the virtual rail 404, the robotic system 110 and/or the control system 150 can determine the alignment positions 180. For example, the alignment positions 180 can represent positions of the third robotic arm 112(C) when a center of the end effector of the third robotic arm 112(C) is aligned to the virtual rail 404, when a center of the end effector of the third robotic arm 112(C) is aligned to the virtual rail 404 with a particular offset (as discussed below in reference to FIG. 9), when another reference point/element of the end effector of the third robotic arm 112(C) is aligned to the virtual rail 404, and so on. In this example, the alignment positions 180 represent positions for a distal end of the third robotic arm 112(C) such that, when the scope 130 is attached to the distal end of the third robotic arm 112(C), the scope 130 is aligned with the virtual rail 404 for insertion/retraction of the scope 130. For ease of illustration, three alignment positions 180 are illustrated. However, it should be understood that the alignment positions 180 represent any number of alignment positions. The virtual rail 404 and the plurality of alignment positions 180 are depicted using dashed lines to indicate that the elements do not depict any physical structure of the medical system 100.

Figure 5:
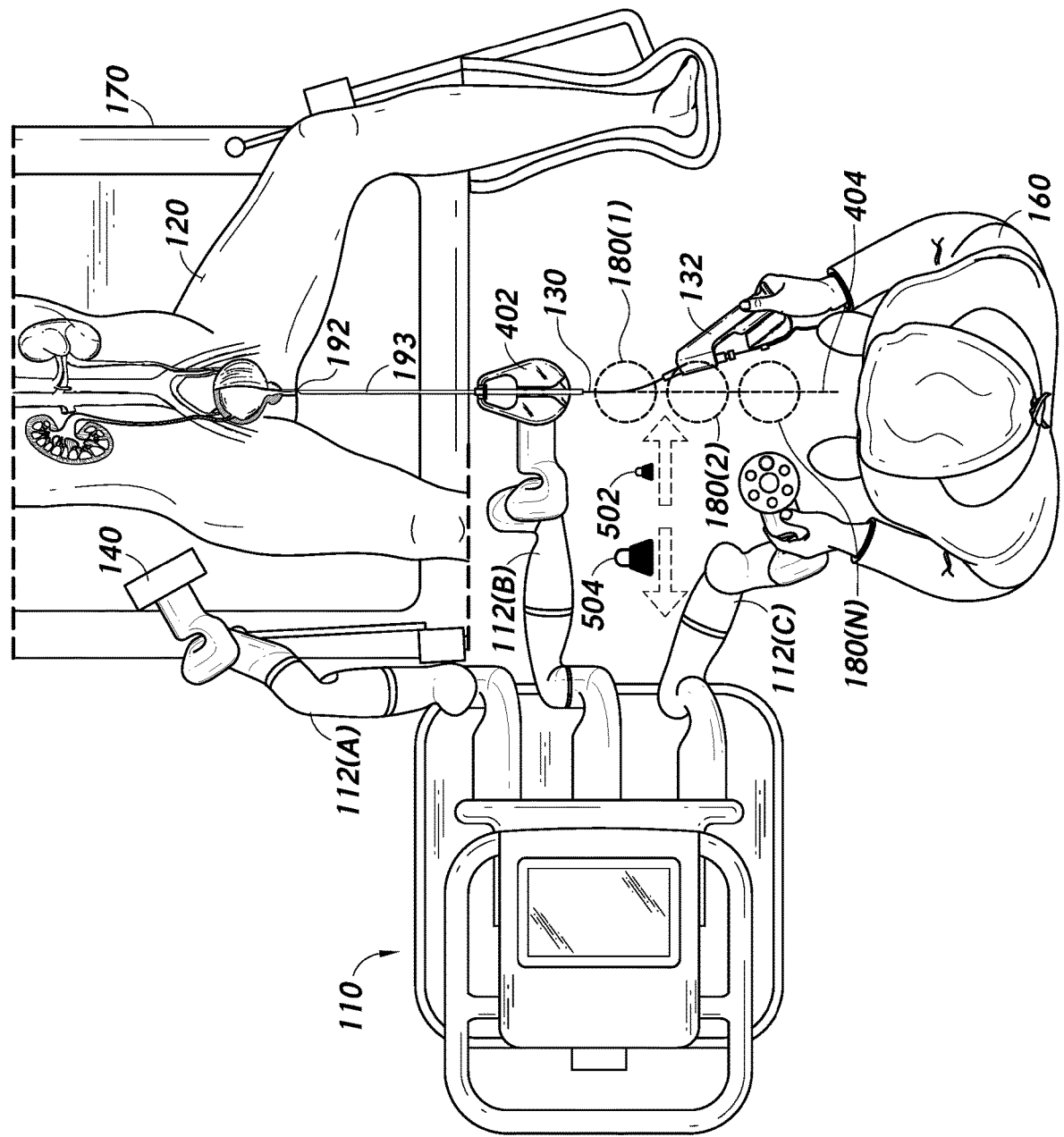
FIG. 5 illustrates an example robotic arm configured to provide varying amounts of resistance for manual movement of the robotic arm in accordance with one or more embodiments.

With the alignment positions 180 determined, the physician 160 can attempt to align the third robotic arm 112(C) to the second robotic arm 112(B). For example, as shown in FIGS. 4 and 5, the physician 160 can hold the handle 132 of the scope 130 with a right hand and grab the third robotic arm 112(C) with a left hand to enable the admittance control mode for the third robotic arm 112(C). The physician 160 can then manually move the third robotic arm 112(C) closer to the handle 132 in an attempt to align the third robotic arm 112(C) to the second robotic arm 112(B) (e.g., based on the alignment positions 180, which are not seen by the physician 160). The handle 132 (also referred to as "the instrument coupling/manipulator 132") can be configured to facilitate advancement and/or operation of a basketing device and/or another medical instrument that can be deployed using the scope 130, such as any instrument deployed through a working channel of the scope 130.

As illustrated in FIG. 5, the third robotic arm 112(C) can be configured to provide varying amounts of resistance for manual movement of the third robotic arm 112(C) relative to the alignment positions 180. In some embodiments, the amount of resistance associated with the third robotic arm 112(C) can be based on a direction in which the third robotic arm 112(C) is being moved. For example, the third robotic arm 112(C) can exhibit a first amount of resistance (illustrated with a weight icon 502) for manual movement of the third robotic arm 112(C) in a direction closer to one or more of the alignment positions 180 with respect to at least one dimension (e.g., X, Y, or Z). In contrast, the third robotic arm 112(C) can exhibit a second amount of resistance (illustrated with a weight icon 504) for manual movement of the third robotic arm 112(C) in a direction farther from one or more of the alignment positions 180 with respect to at least one dimension. In this example, the first amount of resistance is less than the second amount of resistance and/or a threshold, while the second amount of resistance is greater than the first amount of resistance and/or the threshold. As such, the physician 160 can experience a sense of lightness/ease when moving the third robotic arm 112(C) closer to the alignment positions 180 and experience a sense of heaviness/difficulty when moving the third robotic arm 112(C) farther from the alignment positions 180. However, in other examples, the first amount of resistance can be greater than the second amount of resistance (or the same, in some cases). In some instances, as the third robotic arm 112(C) moves closer to the one or more of the alignment positions 180, the first amount of resistance decreases. Further, as the third robotic arm 112(C) moves farther from one or more of the alignment positions 180, the second amount of resistance increases.

In some embodiments, the amount of resistance associated with manual movement of the third robotic arm 112(C) can be based on a proximity of the third robotic arm 112(C) to the alignment positions 180. For example, the amount of resistance can depend on whether or not the distal end of the third robotic arm 112(C) is within a threshold distance to one or more of the alignment positions 180. If, for instance, the third robotic arm 112(C) is within the threshold distance to one or more of the alignment positions 180, the third robotic arm 112(C) can exhibit a first amount of resistance for movement in any direction. In contrast, if the third robotic arm 112(C) is outside the threshold distance to one or more of the alignment positions 180, the third robotic arm 112(C) can exhibit a second amount of resistance for movement in any direction.

The robotic system 110 and/or the control system 150 can generally adjust/configure the amount of resistance for the third robotic arm 112(C) by tracking a location of a distal end of the third robotic arm 112(C). In some instances, the robotic system 110 can generate position/pose information regarding the distal end of the third robotic arm 112(C), which may be provided to the control system 150 to track the third robotic arm 112(C). Based on the tracking, the robotic system 110 and/or the control system 150 can determine a direction in which the third robotic arm 112(C) is moving relative to the alignment positions 180, a proximity of the third robotic arm 112(C) relative to the alignment positions 180, and so on. As such, the robotic system 110 and/or the control system 150 can dynamically update an amount of resistance of the third robotic arm 112(C) for manual movement of the third robotic arm 112(C).

Figure 6:
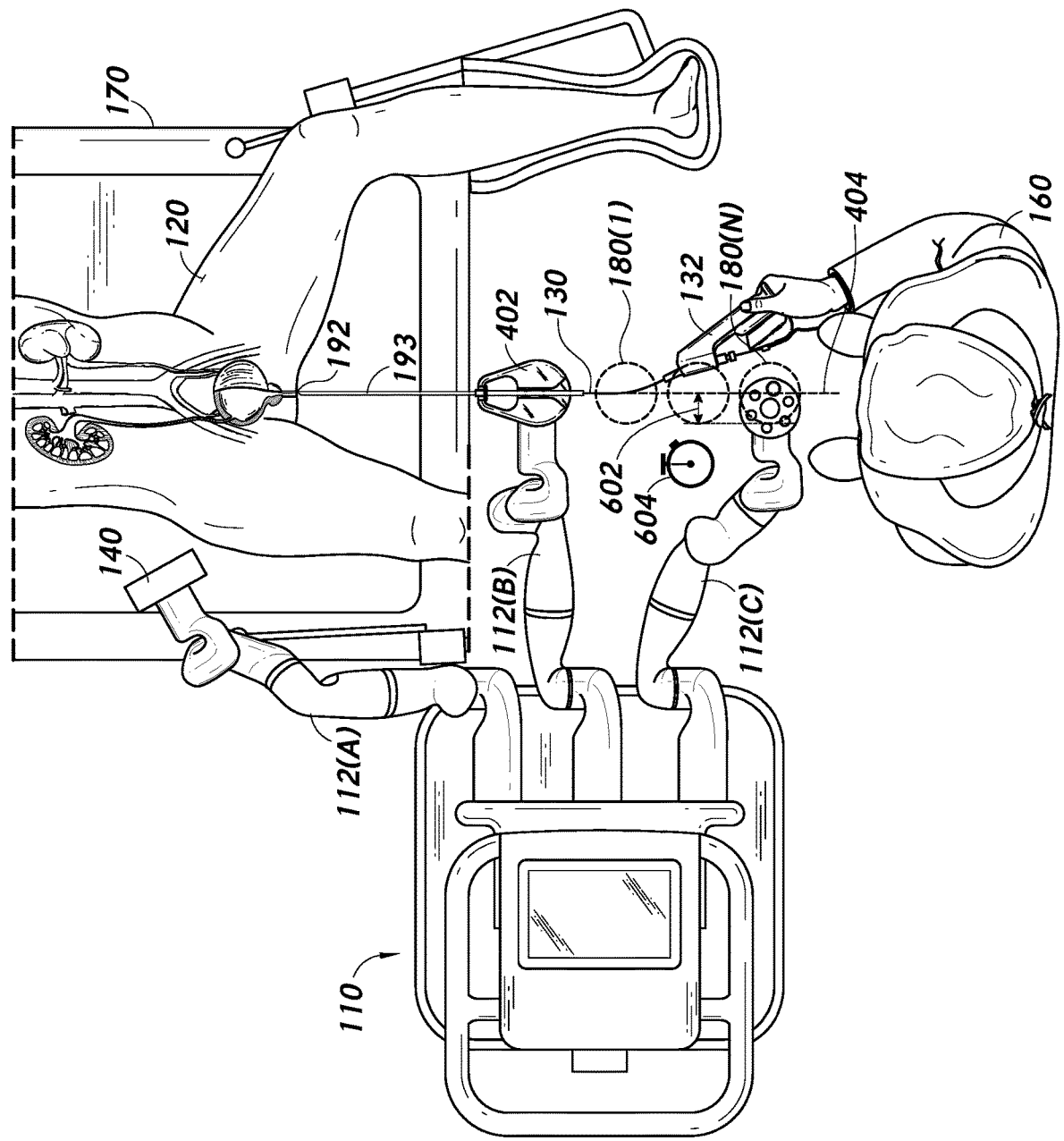
FIG. 6 illustrates an example robotic arm positioned within a threshold distance to an alignment position in accordance with one or more embodiments.

In some embodiments, the robotic system 110 and/or the control system 150 can automatically move one or more of the robotic arms 112 to one or more of the alignment positions 180. For example, the robotic system 110 can determine that the distal end of the third robotic arm 112(C) is positioned within a threshold distance 602 (or at the threshold distance) to the alignment position 180(N), as illustrated in FIG. 6. The threshold distance 602 can be configurable, such as by the physician 160, the robotic system 110, the control system 150, or another user/system. The threshold distance 602 can be set to a variety of distances, such as 5 mm, 10 mm, 20 mm, 30 mm, and so on.

Figure 7:
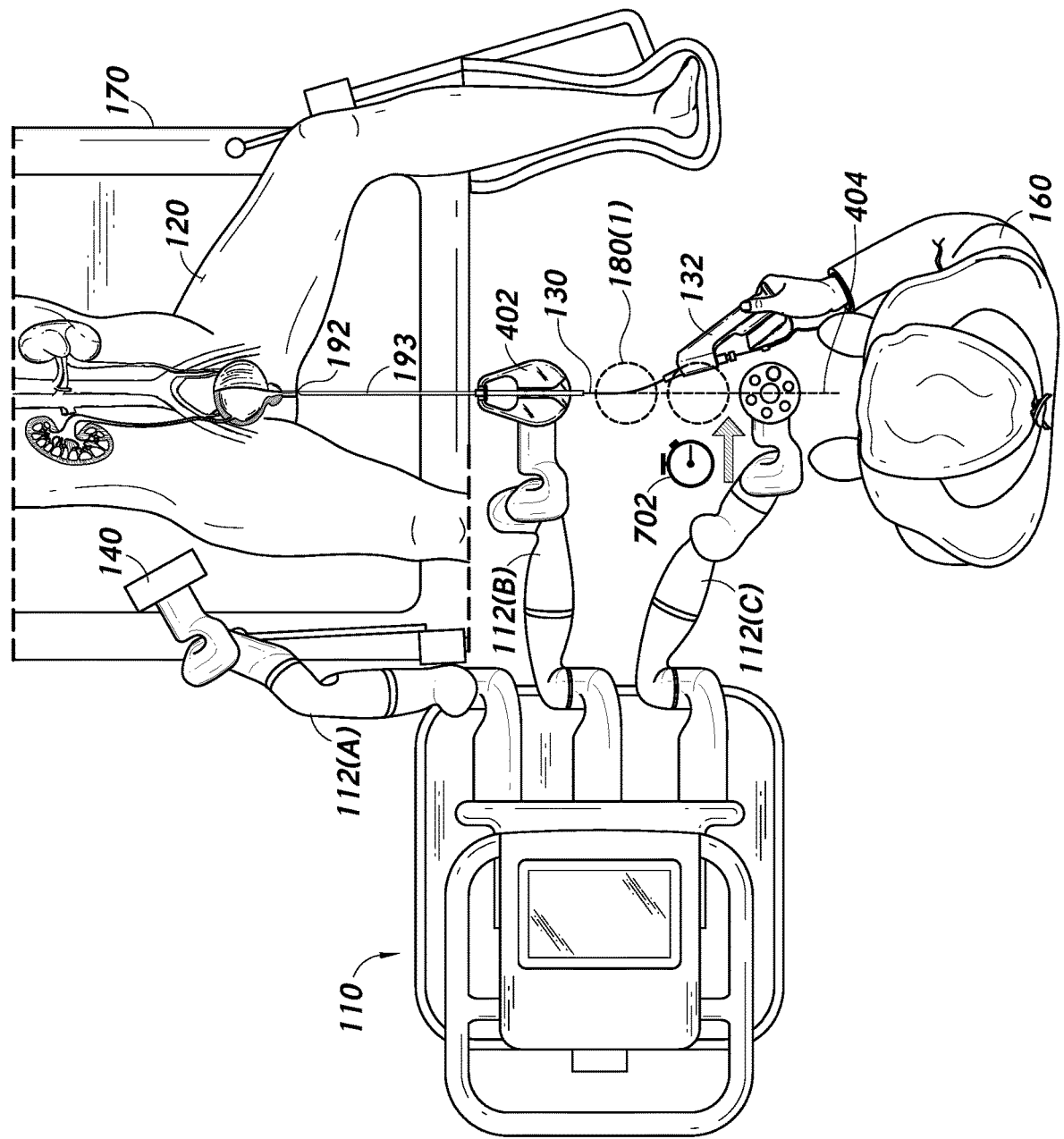
FIG. 7 illustrates an example robotic arm that has been automatically moved to an alignment position in accordance with one or more embodiments.

Additionally, or alternatively, the robotic system 110 can determine that manual movement of the third robotic arm 112(C) has ceased. For example, the robotic system 110 can determine that the admittance control mode for the third robotic arm 112(C) is disabled (e.g., the physician 160 is no longer pressing the admittance control button 312, the physician 160 selects the admittance control button 312 a second time, etc.), the third robotic arm 112(C) is no longer experiencing an external force from the physician 160, the physician 160 has removed his/her hand from the third robotic arm 112(C) (e.g., based on data from a contact/proximity/capacitive sensor), etc. Upon determining that the distal end of the third robotic arm 112(C) is positioned within the threshold distance 602 to the alignment position 180(N) and/or that manual movement of the third robotic arm 112(C) has ceased for more than a period of time (e.g., a predetermined period of time), the robotic system 110 can automatically move the third robotic arm 112(C) to the alignment position 180(N), as shown in FIG. 7. In this example, the third robotic arm 112(C) is moved to the alignment position 180(N) since the third robotic arm 112(C) is within closest proximity to the alignment position 180(N) when manual movement of the third robotic arm 112(C) stopped. A timer icon 604 in FIG. 6 illustrates the start of a timer when manual movement of the third robotic arm 112(C) ceases and a timer icon 702 in FIG. 7 illustrates that a predetermined amount of time has passed from the start of the timer. As such, in some situations where the third robotic arm 112(C) is positioned relatively close to the alignment positions 180, the third robotic arm 112(C) can automatically move into alignment with the second robotic arm 112(B) shortly after (or in response to) the physician 160 releasing the third robotic arm 112(C).

Figure 8:
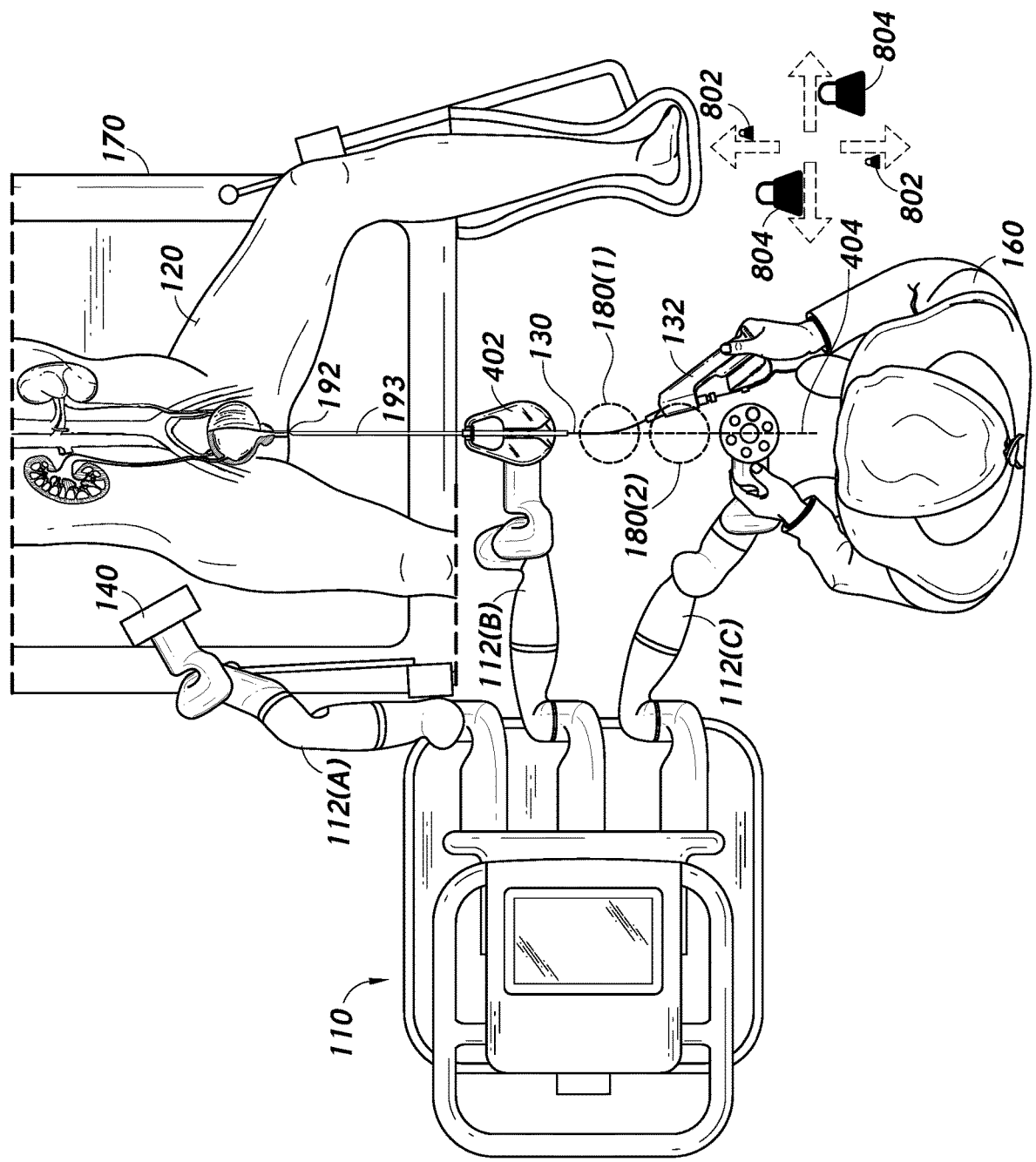
FIG. 8 illustrates an example robotic arm positioned at an alignment positioned and configured to provide varying amounts of resistance in accordance with one or more embodiments.

In some embodiments, the amount of resistance for manual movement of the third robotic arm 112(C) can be adjusted/reconfigured when aligned with one or more of the alignment positions 180, as illustrated in FIG. 8. This can provide an indication to the physician 160 that the third robotic arm 112(C) is aligned and/or avoid manual movement of the third robotic arm 112 from an aligned position. For example, once the third robotic arm 112(C) is aligned with one or more of the alignment positions 180, the third robotic arm 112(C) can be configured to exhibit a first amount of resistance (illustrated with a weight icon 802) for manual movement of the third robotic arm 112(C) from one of the alignment positions 180 to another one of the alignment positions 180 (e.g., along the virtual rail 404). Further, the third robotic arm 112(C) can exhibit a second amount of resistance (illustrated with a weight icon 804) for manual movement of the third robotic arm 112(C) in a direction away from the alignment positions 180 (with respect to at least one dimension). In this example, the first amount of resistance is less than the second amount of resistance and/or a threshold, while the second amount of resistance is greater than the first amount of resistance and/or the threshold. However, in other examples, the first amount of resistance can be greater than the second amount of resistance (or the same, in some cases). As such, the physician 160 can experience a sense of moving along a virtual wall/rail when moving between the alignment positions 180. Due to such resistance changes, the physician 160 can also experience a feeling of locking/snapping the third robotic arm 112(C) into a virtual rail/position when the third robotic arm 112(C) is aligned.

In some embodiments, the amount of resistance for manual movement of the third robotic arm 112(C) within or away from the alignment positions 180 can be different than the amount of resistance for manual movement of the third robotic arm 112(C) before alignment is reached. For example, as discussed above in reference to FIG. 5, the third robotic arm 112(C) can exhibit a first amount of resistance for manual movement of the third robotic arm 112(C) in a direction towards the alignment positions 180 and/or exhibit a second amount of resistance for manual movement of the third robotic arm 112(C) in a direction away from the alignment positions 180. Once the third robotic arm 112(C) is aligned, the third robotic arm 112(C) can exhibit a third amount of resistance for manual movement from one of the alignment positions 180 to another one of the alignment positions 180, wherein the third amount of resistance can be less than the first amount of resistance. As such, the physician 160 can experience a feeling of even greater ease when moving the third robotic arm 112(C) from one alignment position to another alignment position (in comparison to moving toward the alignment positions 180). Further, when the third robotic arm 112(C) is aligned, the third robotic arm 112(C) can exhibit a fourth amount of resistance for manual movement away from the alignment positions 180, wherein the fourth amount of resistance can be greater than the second amount of resistance. As such, the physician 160 can experience a feeling of even greater difficulty when moving the third robotic arm 112(C) from the alignment positions 180 (in comparison to moving away from the alignment positions 180 before the third robotic arm 112(C) is aligned).

As similarly discussed above in reference to FIGS. 6 and 7, in some embodiments, if the third robotic arm 112(C) is moved slightly out of alignment with the second robotic arm 112(B) once aligned, the third robotic arm 112(C) can be automatically moved back into alignment with the second robotic arm 112(B). For example, assume that the physician 160 adjusts the insertion/retraction distance of the third robotic arm 112(C) relative to the second robotic arm 112(B) (e.g., moves the third robotic arm 112(C) substantially along the virtual rail 404). Also, assume that in doing so, the third robotic arm 112(C) is moved slightly out of alignment with the alignment positions 180. Here, if the third robotic arm 112(C) is still within a threshold distance to one or more of the alignment positions 180, the third robotic arm 112(C) can be automatically moved back into alignment with one or more of the alignment positions 180.

Figure 9:
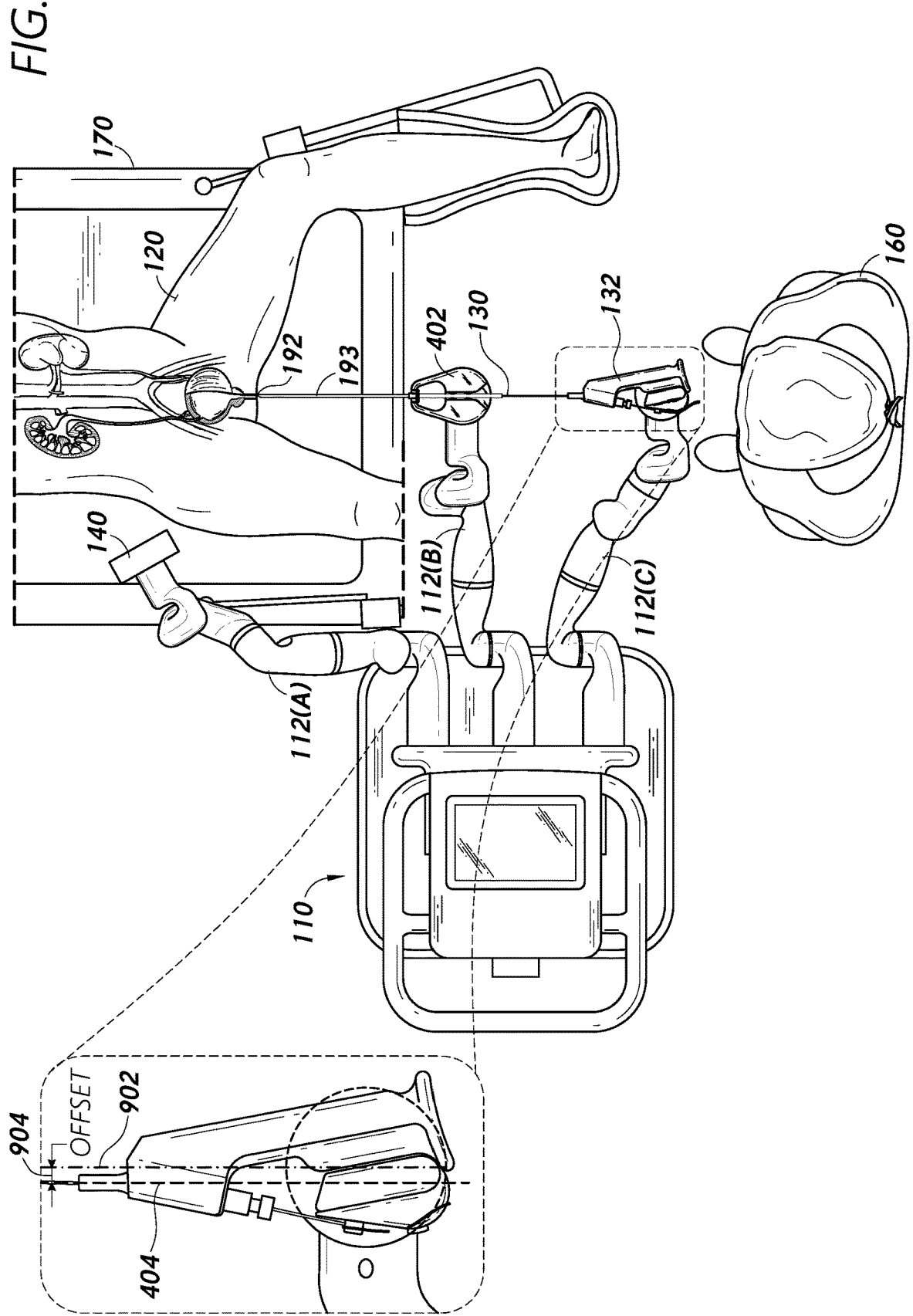
FIG. 9 illustrates an example robotic arm positioned at an alignment position and arranged with a scope attached thereto in accordance with one or more embodiments.

In many embodiments, once the third robotic arm 112(C) is aligned with one or more of the alignment positions 180, the physician 160 can attach to the scope 130 to the third robotic arm 112(C), as shown in FIG. 9. In particular, the physician 160 can attach the handle 132 associated with the scope 130 to the end effector of the third robotic arm 112(C). With the scope 130 attached, the physician 160 can begin the procedure or move on to other phases of a procedure in instances where the scope 130 is attached during a procedure. Once attached, the scope 130 can be retracted/inserted into the patient 120 by moving the third robotic arm 112(C) in a vertical direction with respect to FIG. 9 along the virtual rail 404.

As illustrated in FIG. 9, in some embodiments a center of the end effector of the third robotic arm 112(C) is offset from the virtual rail 404 when the third robotic arm 112(C) is aligned to one or more of the alignment positions 180. This can be due to an offset of the scope 130 relative to the end effector of the third robotic arm 112(C) when the handle 132 is attached to the third robotic arm 112(C) (e.g., an offset in the attachment position). As shown, a line 902 that extends through a center of the end effector of the third robotic arm 112(C) is offset from the virtual rail 404 by a distance 904 when the handle 132 is mounted on the third robotic arm 112(C). With such offset, it may be difficult for the physician 160 to visually align the robotic arms 112(B) and 112(C). For example, it may be difficult for the physician 162 align the end effector of the third robotic arm 112(C) with some amount of offset with respect to the end effector of the second robotic arm 112(B). Thus, the alignment techniques discussed herein can provide assistance to the physician 160 to align the third robotic arm 112(C) with the second robotic arm 112(B) to facilitate insertion/retraction of the scope 130 (once aligned and attached) along a substantially straight path, wherein such alignment can be associated with some amount of offset with respect to the end effectors of the robotic arms 112(B) and 112(C).

In some instances, the techniques discussed herein can enable a user to manually and/or independently move robotic arms to particular positions in an accurate manner to accommodate certain workflows, environments, physician preferences, and/or safety precautions. This can ultimately provide the user with flexibility in moving robotic arms out of and/or into a workspace at various times. In some examples, a workspace around a patient, such as between the legs of a patient, can be relatively compact/small. Moreover, it may be difficult to visually determine if a robotic arm is aligned to a particular position, especially in cases where such alignment is associated with some amount of offset to another device/robotic arm. Thus, the techniques discussed herein can provide the flexibility to accurately move robotic arms into/out of the workspace to one or more alignment positions. Further, such techniques can avoid user interaction with certain I/O devices (e.g., touch screens, controllers, keyboards, mice, displays, etc.) to position the robotic arms and/or to view a position of the robotic arms. Furthermore, the techniques can enable a user to manually position a robotic arm in an accurate manner with one arm, such as when the user is holding a medical instrument with another arm.

Although FIGS. 4-9 are discussed in the context of aligning the third robotic arm 112(C) to the second robotic arm 112(B), the techniques can be implemented in the context of aligning a robotic arm to a previous position of the robotic arm. For example, one or more of the alignment positions 180 can represent a previous position of the third robotic arm 112(C) and the alignment techniques discussed in reference to FIGS. 4-9 (or elsewhere) can be implemented to assist the physician 160 in aligning the third robotic arm 112(C) to one or more of the alignment positions 180. In one illustration, the alignment techniques can be used to position the third robotic arm 112(C) off to the side to provide adequate space for an operation that does not involve the third robotic arm 112(C) and then move the third robotic arm 112(C) back to the previous position. In another illustration, the alignment techniques can be used to change out a medical instrument attached to the third robotic arm 112(C). Here, the third robotic arm 112(C) can be moved from an initial position, a different medical instrument can be attached to the third robotic arm 112(C), and the third robotic arm 112(C) can be realigned to the previous position.

Example Flow Diagram

Figure 10:
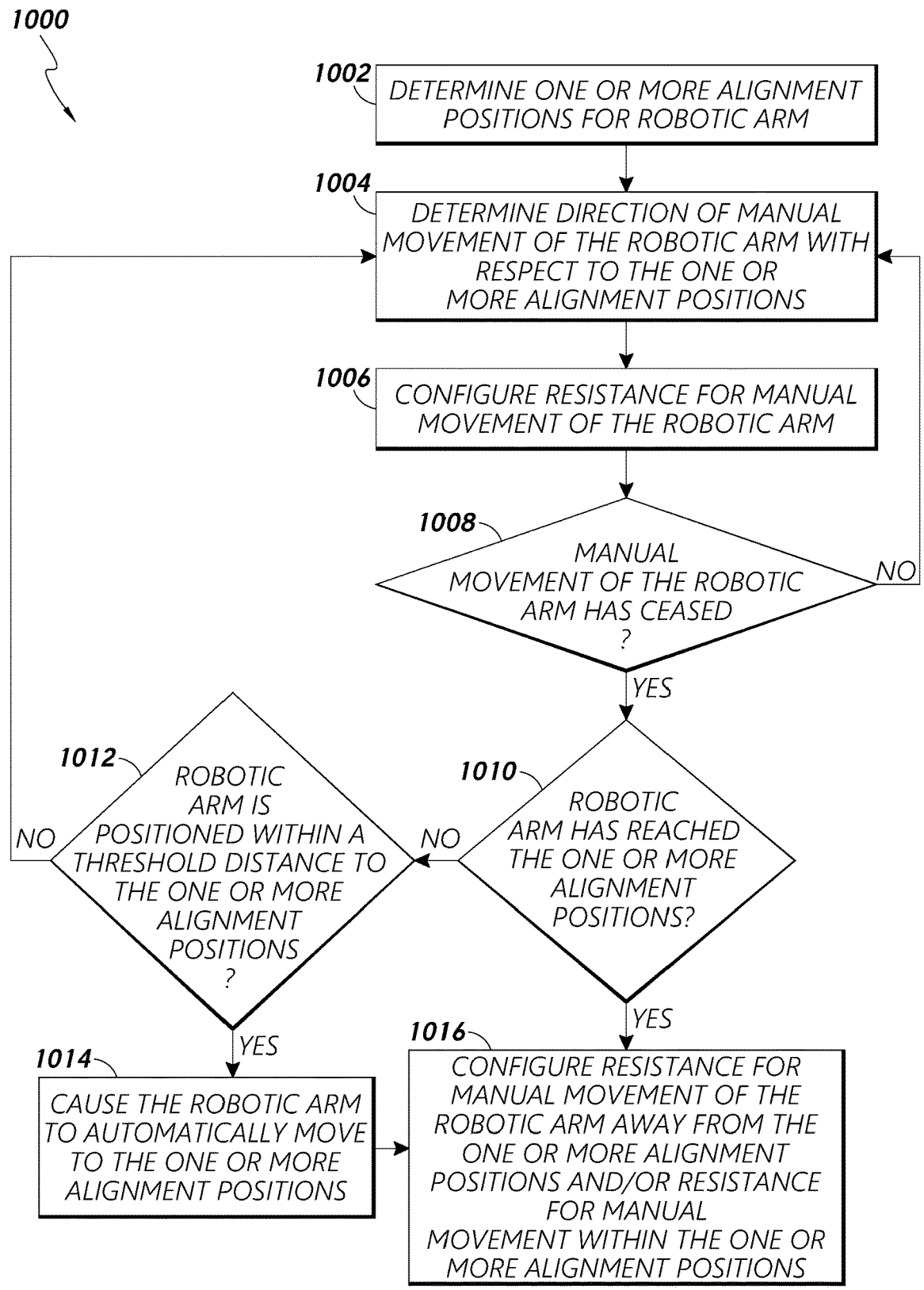
FIG. 10 illustrates an example flow diagram of a process for providing haptic feedback to align a robotic arm in accordance with one or more embodiments.

FIG. 10 illustrates an example flow diagram of a process 1000 for providing haptic feedback to align a robotic arm in accordance with one or more embodiments. The various operations/acts associated with the process 1000 can be performed by control circuitry implemented in any of the devices/systems discussed herein or a combination thereof, such as the control system 150, the robotic system 110, the table 170, a medical instrument, and/or another device. The process 1000 can be performed during setup/configuration of the medical system 100 for a procedure, during a procedure, after a procedure, and/or at other times. In one illustration, the process 1000 is performed to configure the robotic system 110 for a procedure. Although various blocks are illustrated as being part of the process 1000, any of such blocks can be eliminated. Further, additional blocks can be implemented as part of the process 1000. The order in which the blocks are illustrated is provided merely for illustrative purposes, and the blocks can be implemented in any order. In some embodiments, one or more of the blocks of the process 1000 are implemented as executable instructions, that when executed by control circuitry, cause the control circuitry to perform the functionality/operations discussed. However, one or more of the blocks of the process 1000 can be implemented in other manners, such as by other devices/systems, a user(s), etc.

At block 1002, the process 1000 can include determining one or more alignment positions for a robotic arm. In some embodiments, the one or more alignment positions can include a plurality of alignment positions associated with alignment to a distal end of an additional robotic arm. The plurality of alignment positions can be associated with a virtual rail associated with at least one of insertion or retraction of a medical instrument. Further, in some embodiments, the one or more alignment positions represent a previous position of the distal end of the robotic arm.

At block 1004, the process 1000 can include determining a direction of manual movement of the robotic arm with respect to the one or more alignment positions. The direction can be closer to or farther from the one or more alignment positions. For example, position data can be received/generated indicating a current position of the robotic arm (e.g., the distal end of the robotic arm). Based on such position data, and/or position data regarding the one or more alignment positions, the direction of movement of the robotic arm can be determined.

At block 1006, the process 1000 can include configuring (e.g., setting) resistance for manual movement of the robotic arm. The resistance can be configured based on the direction of movement of the distal end of the robotic arm with respect to the one or more alignment positions. For example, a first resistance can be set for manual movement of the robotic arm in a direction closer to the one or more alignment positions with respect to at least one dimension. Further, a second resistance can be set for manual movement of the robotic arm in a direction away from the one or more alignment positions with respect to at least one dimension. The second resistance can be different than the first resistance, such as greater than the first resistance or less than the first resistance.

In some embodiments, the resistance for manual movement of the robotic arm can be decreased as the robotic arm moves closer to the one or more alignment positions (e.g., in response to/based on determining that the robotic arm moves closer to the one or more alignment positions with respect to at least one dimension). Further, in some embodiments, the resistance for manual movement of the robotic arm can be increased as the robotic arm moves farther from the one or more alignment positions (e.g., in response to/based on determining that the robotic arm moves farther from the one or more alignment positions with respect to at least one dimension).

At block 1008, the process 1000 can include determining if manual movement of the robotic arm has ceased (e.g., for more than a predetermined period of time). For example, it can be determined if an admittance control mode for the robotic arm is disabled (e.g., a user is no longer pressing an admittance control button, the user selects the admittance control button a second time, etc.), the robotic arm is no longer experiencing an external force from a user, the user has removed his/her hand from the robotic arm, and so on. If manual movement of the robotic arm has not ceased, the process 1000 can return to block 1004 and loop through blocks 1004-1008 any number of times until manual movement of the robotic arm has ceased. In contrast, if manual movement of the robotic arm has ceased, the process 1000 can proceed to block 1010.

At block 1010, the process 1000 can include determining if the robotic arm has reached the one or more alignment positions. For example, it can be determined if the robotic arm is positioned at one or more of the one or more alignment positions. If the robotic arm has reached the one or more alignment positions, the process 1000 can proceed to block 1016. In contrast, if the robotic arm has not reached the one or more alignment positions, the process 1000 can proceed to block 1012.

At block 1012, the process 1000 can include determining if the robotic arm is positioned within a threshold distance to the one or more alignment positions. For example, position data can be received/generated indicating a current position of the robotic arm. Based on such position data, and/or position data regarding the one or more alignment positions, it can be determined if the robotic arm is positioned within the threshold distance to the one or more alignment positions. If the robotic arm is positioned within the threshold distance to the one or more alignment positions, the process 1000 can proceed to block 1014. In contrast, if the robotic arm is not positioned within the threshold distance to the one or more alignment positions, the process 1000 can return to block 1004.

At block 1014, the process 1000 can include causing the robotic arm to automatically move to the one or more alignment positions. For example, based on determining that manual movement of the robotic arm has ceased and/or determining that the robotic arm is positioned within the threshold distance to the one or more alignment positions, an instruction/request can be generated/sent to control the robotic arm to automatically move to the one or more alignment positions.

At block 1016, the process 1000 can include configuring a resistance for manual movement of the robotic arm away from the one or more alignment positions and/or configuring a resistance for manual movement within the one or more alignment positions. For example, based on determining that the robotic arm has reached the one or more alignment positions and/or the robotic arm automatically moving to the one or more alignment positions, a resistance for manual movement of the robotic arm in a direction away from the one or more alignment positions with respect to at least one dimension can be set. In some examples, such resistance can be greater than a resistance initially associated with manual movement of the robotic arm in a direction away from the one or more alignment positions (e.g., resistance can be increased in comparison to resistance before alignment is reached). However, resistance can be decreased or the same in some cases. Additionally, or alternatively, based on determining that the robotic arm has reached the one or more alignment positions and/or the robotic arm automatically moving to the one or more alignment positions, a resistance for manual movement of the robotic arm from one alignment position to another alignment position can be set. In some examples, such resistance can be less than a resistance initially associated with manual movement of the robotic arm in a direction closer to the one or more alignment positions (e.g., resistance can be decreased in comparison to resistance before alignment is reached). However, resistance can be increased or the same in some cases.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, figure, or description thereof for the purpose of streamlining the disclosure and aiding in the understanding of one or more of the various aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the disclosure herein disclosed and claimed below should not be limited by the particular embodiments described above, but should be determined by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A system comprising:
   a first robotic arm;
   a second robotic arm configured to couple to a medical instrument; and
   control circuitry communicatively coupled to the first robotic arm and the second robotic arm and configured to:
      based at least in part on a position of a distal end of the first robotic arm, determine a plurality of alignment positions for a distal end of the second robotic arm, the plurality of alignment positions associated with a virtual rail that is aligned with the distal end of the first robotic arm;
      set a resistance for manual movement of the second robotic arm based at least in part on a direction of movement of the distal end of the second robotic arm with respect to the plurality of alignment positions;
      determine that manual movement of the second robotic arm has ceased for more than a period of time;
      determine that the distal end of the second robotic arm is positioned within a threshold distance to a first alignment position of the plurality of alignment positions; and
      automatically move the second robotic arm to the first alignment position based at least in part on determining that manual movement of the second robotic arm has ceased for more than the period of time and determining that the distal end of the second robotic arm is positioned within the threshold distance to the first alignment position.

2. The system of claim 1, wherein the virtual rail is associated with at least one of insertion or retraction of the medical instrument.

3. The system of claim 1, wherein at least one of the plurality of alignment positions represents a previous position of the distal end of the second robotic arm.

4. The system of claim 1, wherein the control circuitry is configured to set the resistance for manual movement of the second robotic arm by:
   setting a first resistance for manual movement of the second robotic arm in a direction closer to at least one of the plurality of alignment positions with respect to at least one dimension; and
   setting a second resistance for manual movement of the second robotic arm in a direction away from at least one of the plurality of alignment positions with respect to at least one dimension, the second resistance being greater than the first resistance.

5. The system of claim 4, wherein the control circuitry is further configured to:
   determine that the distal end of the second robotic arm has reached at least one of the plurality of alignment positions; and
   increase the second resistance for manual movement of the second robotic arm in the direction away from at least one of the plurality of alignment positions with respect to at least one dimension.

6. The system of claim 4, wherein the control circuitry is further configured to:
   determine that the distal end of the second robotic arm has reached a first alignment position of the plurality of alignment positions; and
   set a third resistance for manual movement of the second robotic arm from the first alignment position to a second alignment position of the plurality of alignment positions, the third resistance being less than the first resistance.

7. The system of claim 1, wherein the control circuitry is configured to set the resistance for manual movement of the second robotic arm by decreasing the resistance as the second robotic arm moves closer to at least one of the plurality of alignment positions.

8. The system of claim 1, wherein the control circuitry is configured to set the resistance for manual movement of the second robotic arm by increasing the resistance as the second robotic arm moves farther from at least one of the plurality of alignment positions.

9. One or more non-transitory computer-readable media storing computer-executable instructions that, when executed by control circuitry, cause the control circuitry to perform operations comprising:
   based at least in part on a position of a distal end of a first robotic arm, determining a plurality of alignment positions for a distal end of a second robotic arm that is configured to couple to a medical instrument, the plurality of alignment positions representing a virtual rail that is aligned with the distal end of the first robotic arm;
   configuring the second robotic arm to provide a first amount of resistance for manual movement in a direction closer to at least one of the plurality of alignment positions and to provide a second amount of resistance for manual movement in a direction away from at least one of the plurality of alignment positions;
   determining that the second robotic arm is moving farther from at least one of the plurality of alignment positions with respect to at least one dimension; and increasing the second amount of resistance for manual movement of the second robotic arm in the direction away from at least one of the plurality of alignment positions.

10. The one or more non-transitory computer-readable media of claim 9, wherein the operations further comprise:
   determining that manual movement of the second robotic arm has ceased for more than a period of time;
   determining that the distal end of the second robotic arm is positioned within a threshold distance to a first alignment position of the plurality of alignment positions; and
   automatically moving the second robotic arm to the first alignment position based at least in part on the determining that the manual movement of the second robotic arm has ceased for more than the period of time and the determining that the distal end of the second robotic arm is positioned within the threshold distance to first alignment position.

11. The one or more non-transitory computer-readable media of claim 9, wherein the operations further comprise:
   determining that the distal end of the second robotic arm has reached a first alignment position of the plurality of alignment positions; and
   increasing the second amount of resistance for manual movement of the second robotic arm in the direction away from the first alignment position.

12. The one or more non-transitory computer-readable media of claim 9, wherein the operations further comprise:
   determining that the distal end of the second robotic arm has reached a first alignment position of the plurality of alignment positions; and
   configuring the robotic arm to provide a third amount of resistance for manual movement of the robotic arm from the first alignment position to a second alignment position of the plurality of alignment positions, the third amount of resistance being less than the first amount of resistance.

13. A robotic system comprising:
   a robotic arm configured to:
      couple to a medical instrument;
      provide a first amount of resistance for manual movement of the robotic arm in a direction closer to one or more alignment positions, at least one of the one or more alignment positions representing a previous position of a distal end of the robotic arm; and
      provide a second amount of resistance for manual movement of the robotic arm in a direction farther from the one or more alignment positions; and
   control circuitry communicatively coupled to the robotic arm and configured to:
      determine that the robotic arm is moving farther from the one or more alignment positions with respect to at least one dimension; and
      increase the second amount of resistance for manual movement of the robotic arm in the direction away from the one or more alignment positions.

14. The robotic system of claim 13, wherein the one or more alignment positions include a plurality of alignment positions representing a virtual rail associated with at least one of insertion or retraction of the medical instrument.

15. The robotic system of claim 13, wherein the control circuitry is further configured to:
   determine that manual movement of the robotic arm has ceased for more than a period of time;
   determine that a distal end of the robotic arm is positioned within a threshold distance to the one or more alignment positions; and
   cause the robotic arm to automatically move to the one or more alignment positions.

16. The robotic system of claim 13, wherein the control circuitry is further configured to:
   determine that a distal end of the robotic arm has reached the one or more alignment positions; and
   increase the second amount of resistance for manual movement of the robotic arm in the direction away from the one or more alignment positions.

17. The robotic system of claim 13, wherein:
   the one or more alignment positions include a plurality of alignment positions associated with alignment to a distal end of an additional robotic arm of the system;
   the control circuitry is further configured to determine that a distal end of the robotic arm has reached a first alignment position of the plurality of alignment positions; and
   the robotic arm is configured to provide a third amount of resistance for manual movement of the robotic arm from the first alignment position to a second alignment position of the plurality of alignment positions, the third resistance being less than the first amount of resistance.

18. The robotic system of claim 13, wherein the control circuitry is configured to decrease the first amount of resistance as the robotic arm moves closer to the one or more alignment positions.

19. The robotic system of claim 13, wherein the control circuitry is configured to increase the second amount of resistance as the robotic arm moves farther from the one or more alignment positions.

20. A method comprising:
   determining, by control circuitry, one or more alignment positions for a distal end of a robotic arm that is configured to couple to a medical instrument, at least one of the one or more alignment positions representing a previous position of the distal end of the robotic arm;
   configuring, by the control circuitry, the robotic arm to provide a first amount of resistance for manual movement of the robotic arm in a direction closer to the one or more alignment positions and to provide a second amount of resistance for manual movement in a direction away from the one or more alignment positions;
   determining that the distal end of the robotic arm has reached a first alignment position of the one or more alignment positions; and
   configuring the robotic arm to provide a third amount of resistance for manual movement of the robotic arm from the first alignment position to a second alignment position of the one or more alignment positions, the third amount of resistance being less than the first amount of resistance.

21. The method of claim 20, wherein the one or more alignment positions include a plurality of alignment positions associated with alignment to a distal end of an additional robotic arm.

22. The method of claim 20, further comprising:
   determining that the manual movement of the robotic arm has ceased for more than a period of time;
   determining that the distal end of the robotic arm is positioned within a threshold distance to the one or more alignment positions; and
   automatically moving the robotic arm to the one or more alignment positions based at least in part on the determining that the manual movement of the robotic arm has ceased for more than the period of time and the determining that the distal end of the robotic arm is positioned within the threshold distance to the one or more alignment positions.

23. The method of claim 20, wherein the first amount of resistance is less than the second amount of resistance.

24. The method of claim 20, wherein the one or more alignment positions include a plurality of alignment positions associated with alignment to a distal end of an additional robotic arm.

25. A robotic system comprising:
a robotic arm configured to couple to a medical instrument; and
control circuitry communicatively coupled to the robotic arm and configured to:
determine one or more alignment positions for a distal end of the robotic arm;
configure the robotic arm to provide a first amount of resistance for manual movement of the robotic arm in a direction closer to the one or more alignment positions and to provide a second amount of resistance for manual movement in a direction away from the one or more alignment positions;
determine that the distal end of the robotic arm has reached a first alignment position of the one or more alignment positions; and
configure the robotic arm to provide a third amount of resistance for manual movement of the robotic arm from the first alignment position to a second alignment position of the one or more alignment positions, the third amount of resistance being less than the first amount of resistance.

26. The robotic system of claim 25, wherein the one or more alignment positions include a plurality of alignment positions representing a virtual rail associated with at least one of insertion or retraction of the medical instrument.

27. The robotic system of claim 25, wherein the control circuitry is further configured to:
determine that manual movement of the robotic arm has ceased for more than a period of time;
determine that a distal end of the robotic arm is positioned within a threshold distance to the one or more alignment positions; and
cause the robotic arm to automatically move to the one or more alignment positions.

28. The robotic system of claim 25, wherein the control circuitry is further configured to:
determine that a distal end of the robotic arm has reached the one or more alignment positions; and
increase the second amount of resistance for manual movement of the robotic arm in the direction away from the one or more alignment positions.

29. The robotic system of claim 25, wherein the one or more alignment positions include a plurality of alignment positions associated with alignment to a distal end of an additional robotic arm.

30. The robotic system of claim 25, wherein the control circuitry is configured to decrease the first amount of resistance as the robotic arm moves closer to the one or more alignment positions.

* * * * *